United States Patent
De Backer

(10) Patent No.: US 11,109,830 B2
(45) Date of Patent: Sep. 7, 2021

(54) METHOD FOR DETERMINING A RESPIRATORY CONDITION BASED ON FUNCTIONAL RESPIRATORY IMAGING

(71) Applicant: FLUIDDA RESPI, Kontich (BE)

(72) Inventor: Jan De Backer, Brussels (BE)

(73) Assignee: FLUIDDA RESPI

( * ) Notice: Subject to any disclaimer, the term of this patent is extended or adjusted under 35 U.S.C. 154(b) by 135 days.

(21) Appl. No.: 14/760,195

(22) PCT Filed: Feb. 14, 2014

(86) PCT No.: PCT/EP2014/052881
§ 371 (c)(1),
(2) Date: Jul. 9, 2015

(87) PCT Pub. No.: WO2014/125059
PCT Pub. Date: Aug. 21, 2014

(65) Prior Publication Data
US 2015/0351714 A1    Dec. 10, 2015

Related U.S. Application Data

(60) Provisional application No. 61/764,957, filed on Feb. 14, 2013.

(51) Int. Cl.
*A61B 6/00* (2006.01)
*A61B 6/03* (2006.01)
(Continued)

(52) U.S. Cl.
CPC ............ *A61B 6/5217* (2013.01); *A61B 5/085* (2013.01); *A61B 5/087* (2013.01); *A61B 5/091* (2013.01);
(Continued)

(58) Field of Classification Search
CPC .. A61B 5/00; A61B 6/00; A61B 6/517; A61B 6/50; A61B 6/032; A61B 6/03;
(Continued)

(56) References Cited

U.S. PATENT DOCUMENTS

2003/0055331 A1* 3/2003 Kotmel .................. A61B 6/541
600/410
2007/0231779 A1* 10/2007 Santhanam ............ G09B 23/28
434/262
(Continued)

FOREIGN PATENT DOCUMENTS

WO      20101136528 A1    12/2010
WO      WO 2010136528 A1 * 12/2010 ............. A61B 5/085

OTHER PUBLICATIONS

King, Talmadge E., Annie Pardo, and Moisés Selman. "Idiopathic pulmonary fibrosis." The Lancet 378.9807 (2011): 1949-1961.*
(Continued)

*Primary Examiner* — Sean D Mattson
(74) *Attorney, Agent, or Firm* — Lathrop GPM LLP; James H. Velema, Esq.; Gordon R. Moriarty, Esq.

(57) ABSTRACT

A method for determining a respiratory condition or for assessing the efficacy of a treatment for a respiratory condition or for optimizing a treatment protocol for a respiratory condition in a subject comprising the steps of: a) obtaining image data concerning two or more three-dimensional images of the subject's respiratory system, which images have been previously acquired during an assessment period; b) calculating a specific three-dimensional structural model of the subject's respiratory system for each of the two or more three-dimensional images of step a); c) comparing the three-dimensional structural models of step b) with each other to determine a respiratory condition or to assess the
(Continued)

Figure 3B:
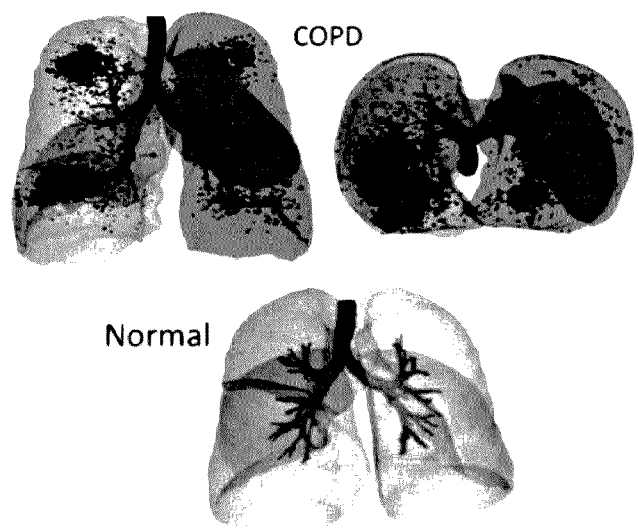

efficacy of a treatment for a respiratory condition or to optimize a treatment protocol for a respiratory condition.

14 Claims, 28 Drawing Sheets

(51) Int. Cl.
| | |
|---|---|
| A61B 5/00 | (2006.01) |
| A61N 5/10 | (2006.01) |
| A61B 5/085 | (2006.01) |
| A61B 5/087 | (2006.01) |
| A61B 5/091 | (2006.01) |
| G06T 7/60 | (2017.01) |
| G06T 7/00 | (2017.01) |
| G16H 50/50 | (2018.01) |

(52) U.S. Cl.
CPC .......... *A61B 5/4839* (2013.01); *A61B 5/4848* (2013.01); *A61B 5/7246* (2013.01); *A61B 5/7282* (2013.01); *A61B 6/032* (2013.01); *A61B 6/50* (2013.01); *A61N 5/10* (2013.01); *G06T 7/0012* (2013.01); *G06T 7/60* (2013.01); *G16H 50/50* (2018.01); *A61B 6/03* (2013.01); *A61B 2576/02* (2013.01); *G06T 2207/10081* (2013.01); *G06T 2207/10088* (2013.01); *G06T 2207/10104* (2013.01); *G06T 2207/30061* (2013.01)

(58) Field of Classification Search
CPC ... A61B 5/7246; A61B 5/4848; A61B 5/4839; A61B 5/7282; A61B 5/085; A61B 5/091; A61B 5/087; A61B 2576/02; G16H 50/50; G06T 7/60; G06T 7/0012; G06T 2207/30061; G06T 2207/10104; G06T 2207/10088; G06T 2207/10081; A61N 5/10
See application file for complete search history.

(56) References Cited

U.S. PATENT DOCUMENTS

| | | | | |
|---|---|---|---|---|
| 2011/0058721 A1* | 3/2011 | Zhang | ............. | A61B 5/08 382/131 |
| 2011/0093243 A1* | 4/2011 | Tawhai | ............. | G06F 17/5018 703/2 |
| 2012/0215504 A1* | 8/2012 | Parker | ............. | A61B 5/083 703/2 |

OTHER PUBLICATIONS

Estenne, Marc, et al. "Detection of obliterative bronchiolitis after lung transplantation by indexes of ventilation distribution." American journal of respiratory and critical care medicine 162.3 (2000): 1047-1051.*

Camargo, Jose JP, et al. "Computed tomography measurement of lung volume in preoperative assessment for living donor lung transplantation: volume calculation using 3D surface rendering in the determination of size compatibility." Pediatric transplantation 13.4 (2009): 429-439.*

Lin, Ching-long, et al. "Computational fluid dynamics." IEEE Engineering in Medicine and Biology Magazine 28.3 (2009): 25-33. (Year: 2009).*

Camargo et al. (2009) "Computed tomography measurement of lung volume in preoperative assessment for living donor lung transplantation: Volume calculation using 3D surface rendering in the determination of size compatibility," Pediatric Transplantation. 13(4):429-439.

De Backer et al. (Nov. 2011) "The effects of long-term noninvasive ventilation in hypercapnic COPD patients: a randomized controlled pilot study," International Journal of Chronic Obstructive Pulmonary Disease. 6:615-624.

Laohaburanakit et al. (2003) "Bronchiolitis obliterans," Clinical Reviews in Allergy and Immunology. 25(3):259-274.

International Preliminary Report on Patentability corresponding to International Patent Application No. PCT/EP2014/052881, dated Aug. 18, 2015.

International Search Report with Written Opinion corresponding to International Patent Application No. PCT/EP2014/052881, dated Jun. 24, 2014.

De Backer et al. (2007) "Functional imaging using computational fluid dynamics to predict treatment success of mandibular advancement devices in sleep-disordered breathing," J. Biomech. 40(16):3708-3714.

De Backer et al. (2008) "Computational fluid dynamics can detect changes in airway resistance in asthmatics after acute bronchodilation," J. Biomech. 41(1)106-113.

De Backer et al. (2008) "Flow analyses in the lower airways: patient-specific model and boundary conditions," Med. Eng Phys. 30(7):872-879.

De Backer et al. (2008) "Novel imaging techniques using computer methods for the evaluation of the upper airway in patients with sleep-disordered breathing: a comprehensive review," Sleep Med. Rev. 12:437-447.

De Backer et al. (2010) "Validation of computational fluid dynamics in CT-based airway models with SPECT/CT," Radiology. 257:854-862.

De Backer et al. (Dec. 19, 2011) "The acute effect of budesonide/formoterol in COPD: a multi-slice computed tomography and lung function study," Eur. Respir. J. 40:298-305.

De Backer et al. (Nov. 22, 2013) "Effect of high-dose N-acetylcysteine on airway geometry, inflammation, and oxidative stress in COPD patients," Int. J. COPD. 8:569-579.

Vinchurkar et al. (Jan. 20, 2012) "A case series on lung deposition analysis of inhaled medication using functional maging based computational fluid dynamics in asthmatic patients: effect of upper airway morphology and comparison with in vivo data," Inhalation Toxicology. 24(2):81-88.

Vos et al. (Apr. 12, 2013) "Novel functional imaging of changes in small airways of patients treated with extrafine beclomethasone/formoterol," Respiration. 86(5):393-401.

* cited by examiner

 
FIG. 1A  FIG. 1B
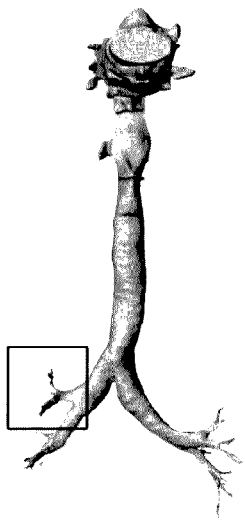 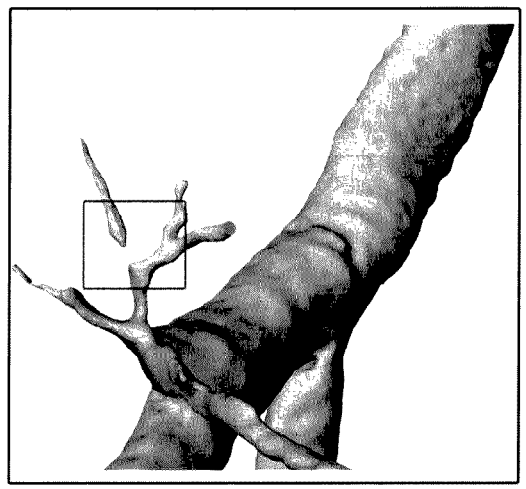
FIG. 2A  FIG. 2B

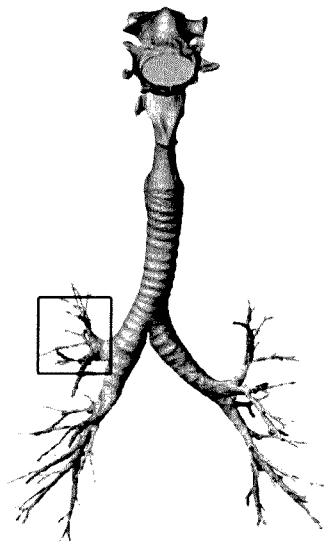 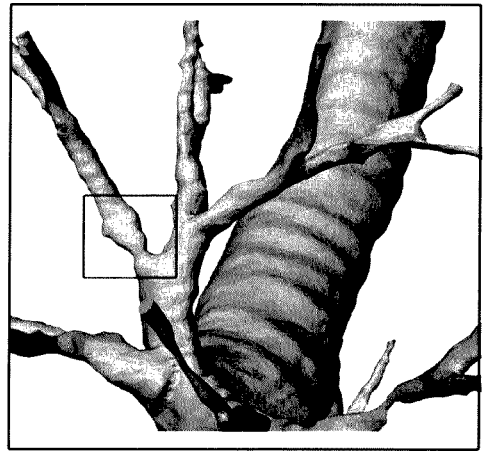
FIG. 2C  FIG. 2D
FIG. 3A

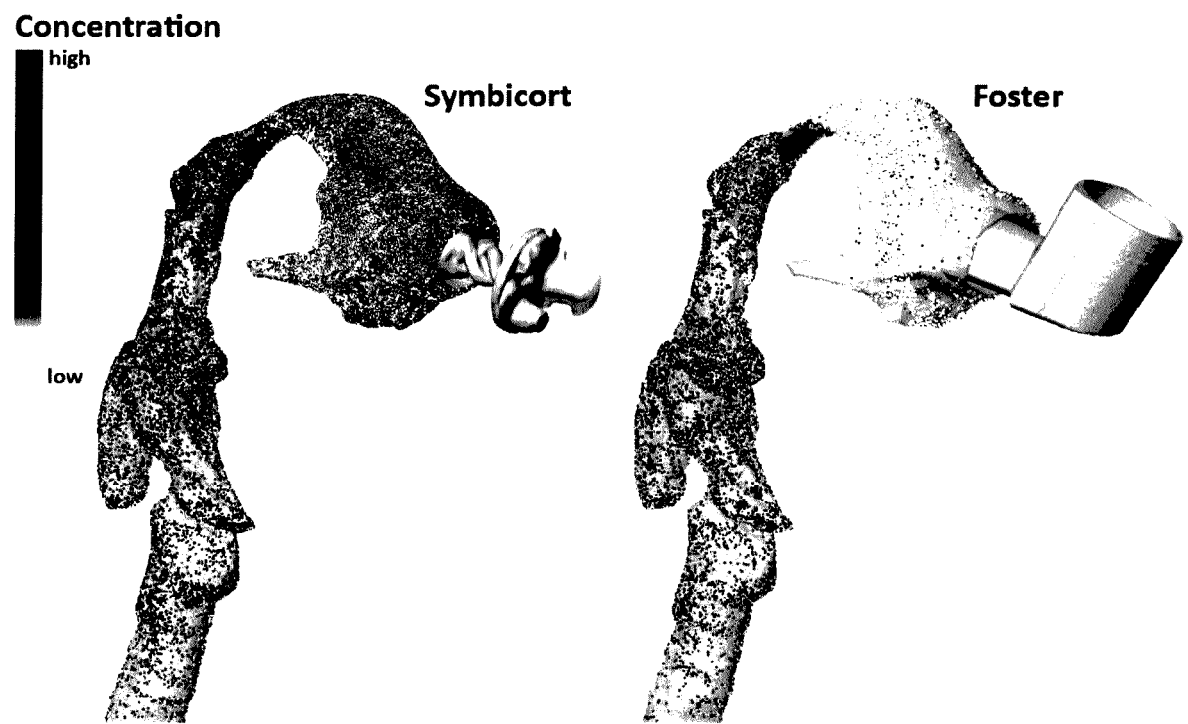
FIG. 8A  FIG. 8B
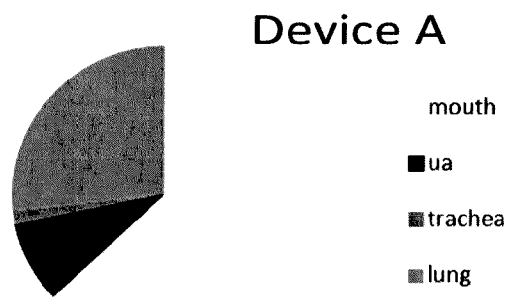 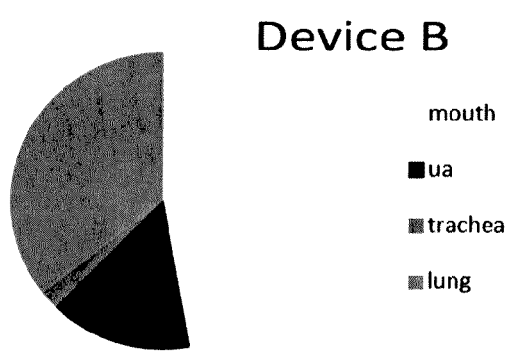
FIG. 8C  FIG. 8D

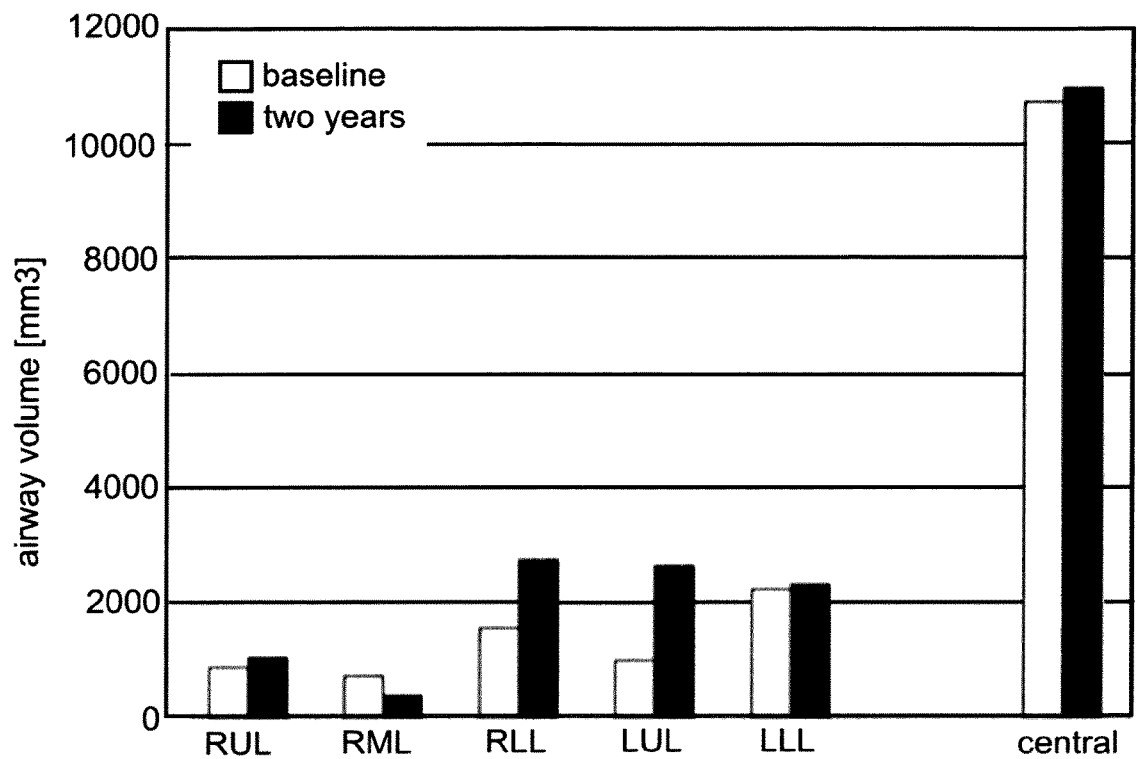
FIG.9E
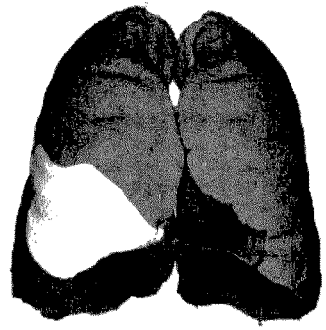
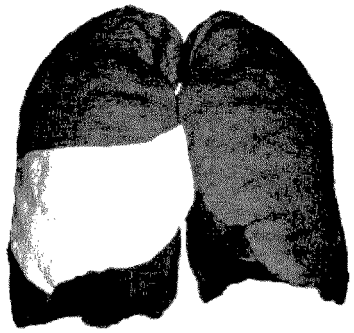
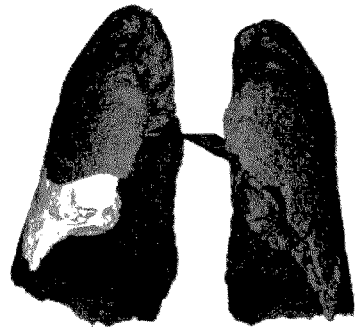
FIG. 10A  FIG. 10B  FIG. 10C healthy

|     | %predicted | Under | Over |
|-----|------------|-------|------|
| RUL | 108.76     | No    | No   |
| RML | 103.95     | No    | No   |
| RLL | 104.41     | No    | No   |
| LUL | 104.79     | No    | No   |
| LLL | 105.66     | No    | No   |

COPD

|     | %predicted | Under | Over |
|-----|------------|-------|------|
| RUL | 120.69     | No    | Yes  |
| RML | 191.07     | No    | Yes  |
| RLL | 93.27      | No    | No   |
| LUL | 131.41     | No    | Yes  |
| LLL | 105.53     | No    | No   |

IPF

|     | %predicted | Under | Over |
|-----|------------|-------|------|
| RUL | 79.00      | Yes   | No   |
| RML | 65.35      | No    | No   |
| RLL | 55.02      | Yes   | No   |
| LUL | 70.46      | Yes   | No   |
| LLL | 63.34      | Yes   | No   |

FIG. 10D

| healthy | | %predicted | Under | Over |
|---|---|---|---|---|
| | RUL | 92.00 | No | No |
| | RML | 99.45 | No | No |
| | RLL | 83.09 | No | No |
| | LUL | 84.10 | No | No |
| | LLL | 78.15 | No | No |

| COPD | | %predicted | Under | Over |
|---|---|---|---|---|
| | RUL | 149.28 | No | Yes |
| | RML | 209.39 | No | Yes |
| | RLL | 123.09 | No | Yes |
| | LUL | 150.84 | No | Yes |
| | LLL | 165.76 | No | Yes |

| IPF | | %predicted | Under | Over |
|---|---|---|---|---|
| | RUL | 58.25 | Yes | No |
| | RML | 42.67 | Yes | No |
| | RLL | 48.04 | Yes | No |
| | LUL | 55.33 | Yes | No |
| | LLL | 63.42 | Yes | No |

FIG. 11D

- Healthy 
- COPD 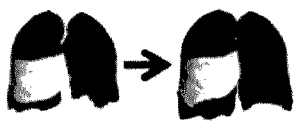
- IPF 
healthy
|  | Lobar expansion [%] | Normal healthy lobar expansion [%] |
|---|---|---|
| RUL | 15.37 | 14.93 |
| RML | 4.67 | 5.81 |
| RLL | 30.84 | 31.68 |
| LUL | 19.06 | 18.34 |
| LLL | 30.06 | 29.24 |
COPD
|  | Lobar expansion [%] | Normal healthy lobar expansion [%] |
|---|---|---|
| RUL | 13.56 | 14.93 |
| RML | 10.66 | 5.81 |
| RLL | 29.47 | 31.68 |
| LUL | 24.34 | 18.34 |
| LLL | 21.97 | 29.24 |
IPF
|  | Lobar expansion [%] | Normal healthy lobar expansion [%] |
|---|---|---|
| RUL | 20.94 | 14.93 |
| RML | 7.49 | 5.81 |
| RLL | 25.68 | 31.68 |
| LUL | 21.41 | 18.34 |
| LLL | 24.48 | 29.24 |
FIG. 12

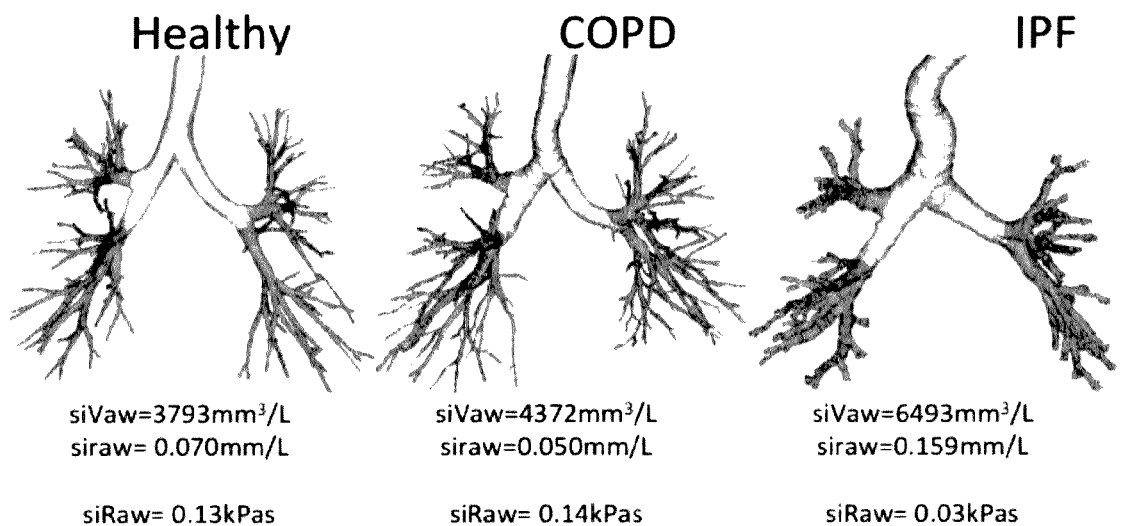
FIG. 13A     FIG. 13B     FIG. 13C
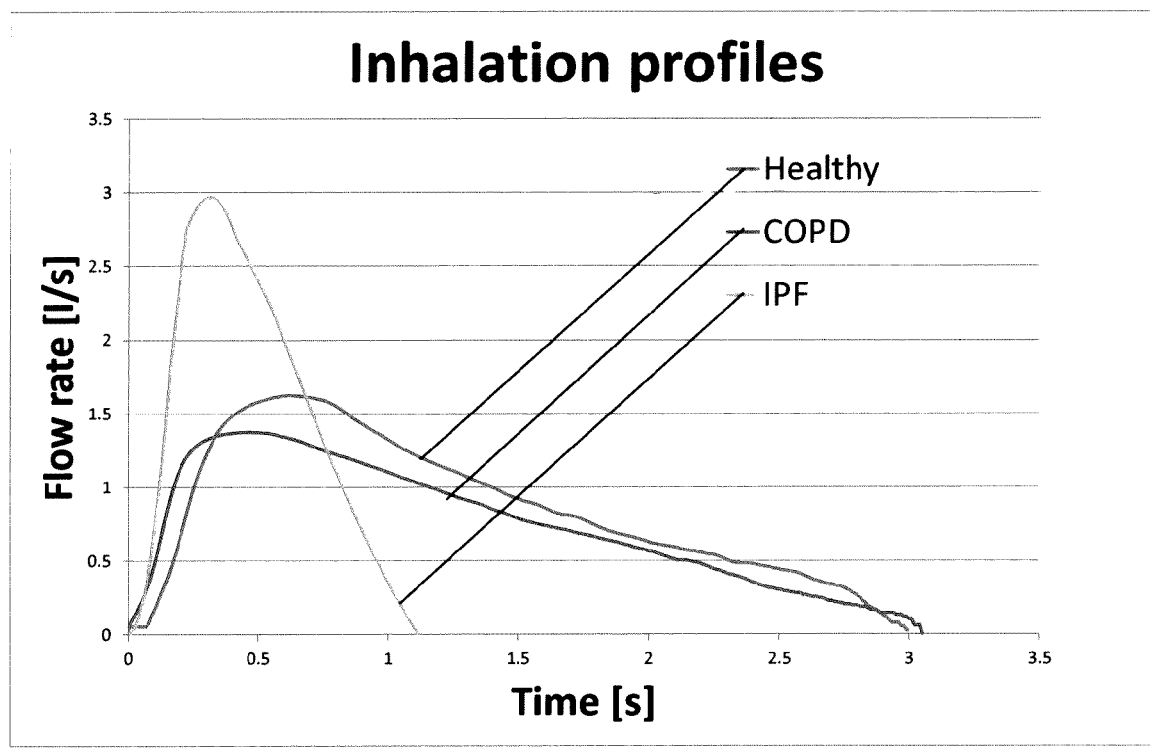
FIG. 14

|  |  | Average [mm3] | SD [mm3] | Correlation | Effect size | Sample size |
|---|---|---|---|---|---|---|
| iVaw | Pre | 2929.120 | 1253.346 | 0.9598713 | 2.157956 | 5 |
|  | Post | 4917.522 | 2054.805 |  |  |  |
| iVaww | Pre | 7863.494 | 3376.762 | 0.9921392 | 1.6430999 | 7 |
|  | post | 6817.392 | 2874.004 |  |  |  |

FIG. 24

METHOD FOR DETERMINING A RESPIRATORY CONDITION BASED ON FUNCTIONAL RESPIRATORY IMAGING

RELATED APPLICATIONS

This application is a 35 U.S.C. § 371 filing of International Application No. PCT/EP2014/052881, filed Feb. 14, 2014, which claims priority to U.S. Patent Application No. 61/764,957, filed Feb. 14, 2013, each of which is incorporated herein by reference in its entirety.

FIELD OF THE INVENTION

The present invention is in the field of respiratory conditions.

BACKGROUND TO THE INVENTION

Respiratory conditions are conditions that result in reduced gaseous exchange. Non-limiting examples of such respiratory conditions include: lung transplantation, radiotherapy, cystic fibrosis (CF), idiopathic pulmonary fibrosis (IPF), chronic obstructive pulmonary disease (COPD), and asthma. Respiratory conditions can be evaluated by using pulmonary function tests (PFTs).

Spirometry (meaning the measuring of breath) is the most common of the pulmonary function tests, measuring lung function, specifically the amount (volume) and/or speed (flow) of air that can be inhaled and exhaled. Spirometry is an important tool used for generating pneumotachographs, which are helpful in assessing respiratory conditions. For example, the FEV1% value is often used as a parameter. FEV1% (FEV1/FVC) is the ratio of FEV1 to FVC. In healthy adults this should be approximately 75-80%. In obstructive diseases (asthma, COPD, chronic bronchitis, emphysema) FEV1 is diminished because of increased airway resistance to expiratory flow; the FVC may be decreased as well, due to the premature closure of airway in expiration, just not in the same proportion as FEV1 (for instance, both FEV1 and FVC are reduced, but the former is more affected because of the increased airway resistance). This generates a reduced value (<80%, often ~45%). However, in restrictive diseases (such as pulmonary fibrosis) the FEV1 and FVC are both reduced proportionally and the value may be normal or even increased as a result of decreased lung compliance.

Because the limited sensitivity of current pulmonary function tests, such as FEV1, it can be very difficult to demonstrate the efficacy of novel compounds, which results in a high number of patients that are needed in clinical trials. Not only does this increase the cost of development of new respiratory drugs, it makes it also difficult to demonstrate bioequivalence of generics.

Therefore, it is an object of the invention to provide an improved method for determining a respiratory condition in a subject. It is also an object of the invention to provide an improved method for assessing the efficacy of a treatment of a respiratory condition. It is also an object of the invention to provide an improved method for optimizing a treatment protocol of a respiratory condition. It is also an object of the invention to provide an improved method that allows a reduction in number of patients needed for clinical trials. It is also an object of the invention to provide an improved method that allows a more efficient and cheaper demonstration of bioequivalence.

SUMMARY OF SOME EMBODIMENTS OF THE INVENTION

The present invention provides a method for determining a respiratory condition in a subject or for assessing the efficacy of a treatment for a respiratory condition or for optimizing a treatment protocol for a respiratory condition, the method comprising the steps of:
a) obtaining image data concerning two or more three-dimensional images of the subject's respiratory system, which images have been previously acquired during an assessment period;
b) calculating a specific three-dimensional structural model of the subject's respiratory system for each of the two or more three-dimensional images of step a);
c) comparing the three-dimensional structural models of step b) with each other to determine a respiratory condition or to assess the efficacy of a treatment for a respiratory condition or to optimize a treatment protocol for a respiratory condition; preferably wherein the assessment period comprises a breathing cycle and the image data of step a) comprise computer tomography, CT, images at functional residual capacity, FRC, and at total lung capacity, TLC, preferably high-resolution CT images at FRC and TLC; or preferably wherein the assessment period comprises pre- and post-treatment stages and the image data of step a) comprise pre- and post-treatment images, preferably high-resolution pre- and post-treatment CT images.

In a preferred embodiment, the invention provides a method as described above, wherein step b) comprises the step b') calculating one or more outcome parameters from the specific three-dimensional structural model of the subject's respiratory system; and wherein step c) comprises the step c') comparing the outcome parameters for each of the data obtained in step a) to determine a respiratory condition or to assess the efficacy of a treatment for a respiratory condition or to optimize a treatment protocol for a respiratory condition;

preferably wherein the specific three-dimensional structural model of the subject's respiratory system comprises a three-dimensional structural model of the subject's lobar structure and a three-dimensional structural model of the subject's airway structure, and wherein step b') further comprises the following steps:

b'') modeling by a computer, the air flow through the airway, using the three-dimensional structural model of the subject's lobar structure and the three-dimensional structural model of the subject's airway structure; and b''') optionally, modeling by a computer, the structural behavior of the airway and the interaction with the flow, using the three-dimensional structural model of the subject's lobar structure and the three-dimensional structural model of the subject's airway structure;

preferably wherein the modeling of step b'') comprises computational fluid dynamics (CFD), comprising solving the Navier-Stokes equations numerically;

preferably wherein the three-dimensional structural model of the subject's lobar structure is used to determine boundary conditions for the computational fluid dynamics; preferably wherein:

the specific three-dimensional structural model of the subject's respiratory system further comprises a three-dimensional structural model of the subject's lung structure at TLC and FRC; and the specific three-dimensional structural model of the subject's respiratory system comprises a three-dimensional structural model of the subject's lobar structure at TLC and FRC;
wherein this specific three-dimensional structural model of the subject's respiratory system is used to determine mass flow rate towards each lobe, and subsequently to obtain the boundary conditions for said computational fluid dynamics.

In a preferred embodiment, the invention provides a method as described above, wherein the one or more outcome parameters comprise the lobar volume, preferably at FRC and TLC; or wherein the one or more outcome parameters comprise the airway volume, preferably at FRC and TLC; or wherein the one or more outcome parameters comprise lobar emphysema; or wherein the one or more outcome parameters comprise lobar blood vessel volume; or wherein the one or more outcome parameters comprise the airway wall thickness; or wherein the one or more outcome parameters comprise the airway resistance, preferably at FRC and TLC; or wherein the one or more outcome parameters comprise the airway volume and/or resistance. In a preferred embodiment, the invention provides a method as described above, wherein the one or more outcome parameters comprise the lobar volume, preferably at FRC and TLC; or wherein the one or more outcome parameters comprise the airway volume, preferably at FRC and TLC; or wherein the one or more outcome parameters comprise the airway wall thickness; or wherein the one or more outcome parameters comprise the airway resistance, preferably at FRC and TLC; or wherein the one or more outcome parameters comprise the airway volume and/or resistance. In a preferred embodiment, the invention provides a method as described above, wherein the one or more outcome parameters comprise aerosol deposition characteristics, such as effective lung dose. In a preferred embodiment, the invention provides a method as described above, wherein the respiratory condition is related to a lung transplantation. In a preferred embodiment, the invention provides a method as described above, wherein method comprises geometrical matching of donor/receptor, preferably by comparing an outcome parameter as defined above, preferably wherein the outcome parameter comprises the lobar volume, preferably at FRC and TLC; or wherein the outcome parameter comprises the airway volume, preferably at FRC and TLC; or wherein the outcome parameter comprises the airway resistance, preferably at FRC and TLC. In a preferred embodiment, the invention provides a method as described above, wherein method comprises detection of bronchiolitis obliterans (BOS), preferably by comparing an outcome parameter as defined in claim 3, preferably wherein the outcome parameter comprises the lobar volume, preferably at FRC and TLC; or wherein the outcome parameter comprises the airway volume, preferably at FRC and TLC; or wherein the outcome parameter comprises lobar blood vessel volume; or wherein the outcome parameter comprises the airway wall thickness; or wherein the outcome parameter comprises the airway resistance, preferably at FRC and TLC; or wherein the outcome parameter comprises the airway volume and/or resistance.

In a preferred embodiment, the invention provides a method as described above, wherein the respiratory condition is related to radiotherapy. In a preferred embodiment, the invention provides a method as described above, wherein the respiratory condition is related to cystic fibrosis. In a preferred embodiment, the invention provides a method as described above, wherein the respiratory condition is related to idiopathic pulmonary fibrosis (IPF). In a preferred embodiment, the invention provides a method as described above, wherein the respiratory condition is related to chronic obstructive pulmonary disease (COPD). In a preferred embodiment, the invention provides a method as described above, wherein the respiratory condition is related to asthma. In a preferred embodiment, the invention provides a method as described above, wherein the method comprises detection of lung functional decline or regional lung functional decline, preferably by comparing an outcome parameter as defined above. In a preferred embodiment, the invention provides a method as described above, wherein the method comprises optimization of an inhalation treatment, preferably by comparing an outcome parameter as defined above.

The invention further provides a method for determining a respiratory condition in a subject or for assessing the efficacy of a treatment for a respiratory condition or for optimizing a treatment protocol for a respiratory condition, the method comprising the steps of:
a) obtaining image data concerning two or more three-dimensional images of the subject's respiratory system, which images have been previously acquired during an assessment period;
b) calculating a specific three-dimensional structural model of the subject's respiratory system from each of the data obtained in step a);
c) comparing the three-dimensional structural models of the subject's respiratory system for each of the image data obtained in step a) to determine a respiratory condition or to assess the efficacy of a treatment for a respiratory condition or to optimize a treatment protocol for a respiratory condition. In other words, the invention provides a method for determining a respiratory condition in a subject or for assessing the efficacy of a treatment for a respiratory condition or for optimizing a treatment protocol for a respiratory condition, the method comprising the steps of:
a) obtaining image data concerning two or more three-dimensional images of the subject's respiratory system, which images have been previously acquired during an assessment period;
b) calculating a specific three-dimensional structural model of the subject's respiratory system for each of the two or more three-dimensional images of step a);
c) comparing the three-dimensional structural models of step b) with each other to determine a respiratory condition or to assess the efficacy of a treatment for a respiratory condition or to optimize a treatment protocol for a respiratory condition.

In a preferred embodiment, the invention provides a method as described above for determining a respiratory condition.

In a preferred embodiment, the invention provides a method as described above for assessing the efficacy of a treatment of a respiratory condition or for optimizing a treatment protocol of a respiratory condition.

In a preferred embodiment, the invention provides a method as described above, wherein the image data of step a) were previously acquired using a CT or MRI scan.

In a preferred embodiment, the invention provides a method as described above, wherein the image data of step a) comprise CT images at FRC and TLC, preferably high-resolution CT images at FRC and TLC.

In a preferred embodiment, the invention provides a method as described above, wherein the structural model of step b) is calculated using segmentation principles.

In a preferred embodiment, the invention provides a method as described above, wherein the specific three-dimensional structural model of the subject's respiratory system comprises a three-dimensional structural model of the subject's lung structure.

In a preferred embodiment, the invention provides a method as described above, wherein the specific three-dimensional structural model of the subject's respiratory system comprises a three-dimensional structural model of the subject's lobar structure.

In a preferred embodiment, the invention provides a method as described above, wherein the structural model of step b) is calculated using lobar segmentation.

In a preferred embodiment, the invention provides a method as described above, wherein the specific three-dimensional structural model of the subject's respiratory system comprises a three-dimensional structural model of the subject's airway structure.

In a preferred embodiment, the invention provides a method as described above, wherein the specific three-dimensional structural model of the subject's respiratory system comprises a three-dimensional structural model of the subject's blood vessel structure.

In a preferred embodiment, the invention provides a method as described above, wherein the specific three-dimensional structural model of the subject's respiratory system comprises a three-dimensional structural model of the subject's airway wall structure.

In a preferred embodiment, the invention provides a method as described above, wherein the specific three-dimensional structural model of the subject's respiratory system comprises a three-dimensional structural model of the subject's emphysematous regions.

In a preferred embodiment, the invention provides a method as described above, wherein step b) comprises the step b') calculating one or more outcome parameters from the specific three-dimensional structural model of the subject's respiratory system; and wherein step c) comprises the step c') comparing the outcome parameters for each of the data obtained in step a) to determine a respiratory condition or to assess the efficacy of a treatment for a respiratory condition or to optimize a treatment protocol for a respiratory condition.

In a preferred embodiment, the invention provides a method as described above, wherein the specific three-dimensional structural model of the subject's respiratory system comprises a three-dimensional structural model of the subject's lobar structure and a three-dimensional structural model of the subject's airway structure, and wherein step b') further comprises the following steps:

b") modeling by a computer, the air flow through the airway, using the three-dimensional structural model of the subject's lobar structure and the three-dimensional structural model of the subject's airway structure; and b'") optionally, modeling by a computer, the structural behavior of the airway and the interaction with the flow, using the three-dimensional structural model of the subject's lobar structure and the three-dimensional structural model of the subject's airway structure.

In a preferred embodiment, the invention provides a method as described above, wherein the modeling of step b") comprises computational fluid dynamics (CFD), comprising solving the Navier-Stokes equations numerically.

In a preferred embodiment, the invention provides a method as described above, wherein the three-dimensional structural model of the subject's lobar structure is used to determine boundary conditions for the computational fluid dynamics.

In a preferred embodiment, the invention provides a method as described above, wherein:
the specific three-dimensional structural model of the subject's respiratory system further comprises a three-dimensional structural model of the subject's lung structure at TLC and FRC; and
the specific three-dimensional structural model of the subject's respiratory system comprises a three-dimensional structural model of the subject's lobar structure at TLC and FRC;
wherein this specific three-dimensional structural model of the subject's respiratory system is used to determine mass flow rate towards each lobe, and subsequently to obtain the boundary conditions for said computational fluid dynamics.

In a preferred embodiment, the invention provides a method as described above, wherein the one or more outcome parameters comprise the lobar volume, preferably at FRC and TLC. In a preferred embodiment, the invention provides a method as described above, wherein the one or more outcome parameters comprise the airway volume, preferably at FRC and TLC. In a preferred embodiment, the invention provides a method as described above wherein the one or more outcome parameters comprise lobar emphysema. In a preferred embodiment, the invention provides a method as described above, wherein the one or more outcome parameters comprise lobar blood vessel volume. In a preferred embodiment, the invention provides a method as described above, wherein the one or more outcome parameters comprise the airway wall thickness. In a preferred embodiment, the invention provides a method as described above, wherein the one or more outcome parameters comprise the airway resistance, preferably at FRC and TLC. In a preferred embodiment, the invention provides a method as described above, wherein the one or more outcome parameters comprise the airway volume and/or resistance.

In a preferred embodiment, the invention provides a method as described above, wherein the one or more outcome parameters comprise aerosol deposition characteristics, such as effective lung dose. In a preferred embodiment, the invention provides a method as described above, wherein the respiratory condition is related to a lung transplantation. In a preferred embodiment, the invention provides a method as described above, wherein method comprises geometrical matching of donor/receptor. In a preferred embodiment, the invention provides a method as described above, wherein method comprises detection of bronchiolitis obliterans (BOS). In a preferred embodiment, the invention provides a method as described above, wherein the method comprises optimization of an inhalation treatment. In a preferred embodiment, the invention provides a method as described above, wherein the respiratory condition is related to radiotherapy. In a preferred embodiment, the invention provides a method as described above, wherein the method comprises detection of radiation pneumonitis and/or fibrosis. In a preferred embodiment, the invention provides a method as described above, wherein the method comprises optimization of an inhalation treatment. In a preferred embodiment, the invention provides a method as described above, wherein the respiratory condition is related to cystic fibrosis. In a preferred embodiment, the invention provides a method as described above, wherein the method comprises detection of lung functional decline or regional lung functional decline. In a preferred embodiment, the invention provides a method as described above, wherein the method comprises optimization of an inhalation treatment.

In a preferred embodiment, the invention provides a method as described above, wherein the respiratory condition is related to idiopathic pulmonary fibrosis (IPF). In a preferred embodiment, the invention provides a method as described above, wherein the method comprises detection of lung functional decline or regional lung functional decline. In a preferred embodiment, the invention provides a method as described above, wherein the method comprises optimization of an inhalation treatment.

In a preferred embodiment, the invention provides a method as described above, wherein the respiratory condition is related to chronic obstructive pulmonary disease (COPD). In a preferred embodiment, the invention provides a method as described above, wherein the method comprises detection of lung functional decline or regional lung functional decline. In a preferred embodiment, the invention provides a method as described above, wherein the method comprises optimization of an inhalation treatment. In a preferred embodiment, the invention provides a method as described above, wherein the respiratory condition is related to asthma. In a preferred embodiment, the invention provides a method as described above, wherein the method comprises detection of lung functional decline or regional lung functional decline. In a preferred embodiment, the invention provides a method as described above, wherein the method comprises optimization of an inhalation treatment. In a preferred embodiment, the invention provides a method as described above, wherein the method is provided as an online service.

The invention also provides a computer program, or a computer program product directly loadable into the internal memory of a computer, or a computer program product stored on a computer-readable medium, or a combination of such computer programs or computer program products, for performing a method as described above.

FIGURE LEGENDS

FIG. 1A-B: Lobar volumes at expiration (FRC), FIG. 1A, and inspiration (TLC), FIG. 1B.

FIG. 2A-D: Airway segmentation at expiration, FIGS. 2A and 2B, and inspiration, FIGS. 2C and 2D.

FIG. 3A-B: Assessment of emphysematous regions on lobar level through the analysis of air voxel interconnectivity.

Figure 4:
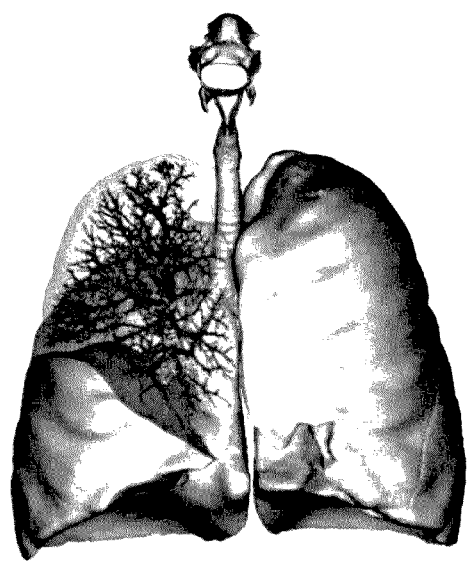

FIG. 4: Lobar blood vessel segmentation.

Figure 5:
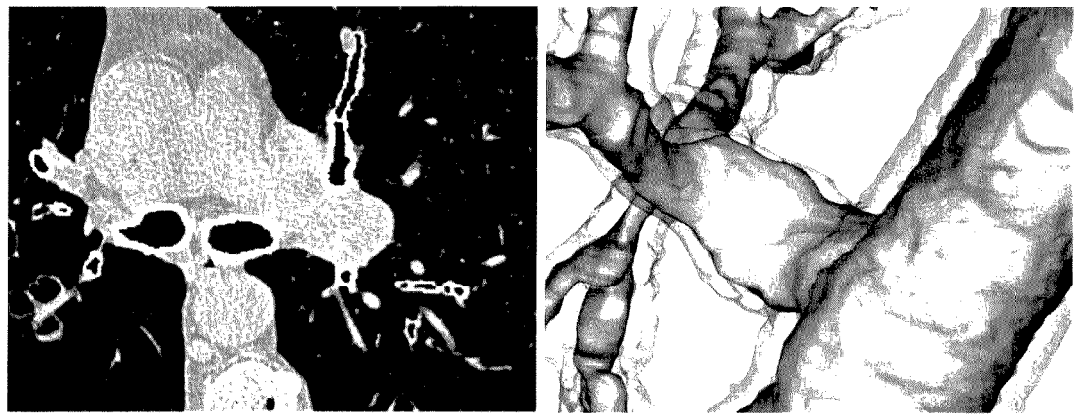

FIG. 5: Airway wall thickness assessment.

Figure 6:
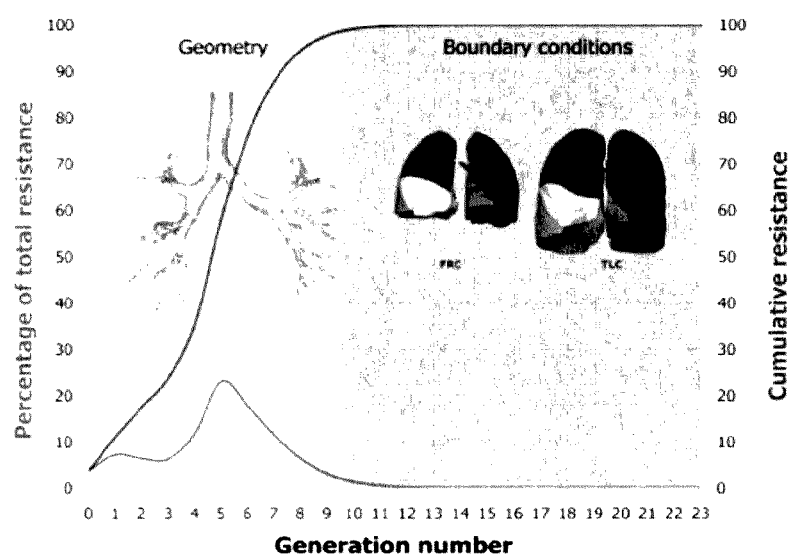

FIG. 6: Assessment of airway resistance using computational fluid dynamics and patient specific boundary conditions.

Figure 7A:
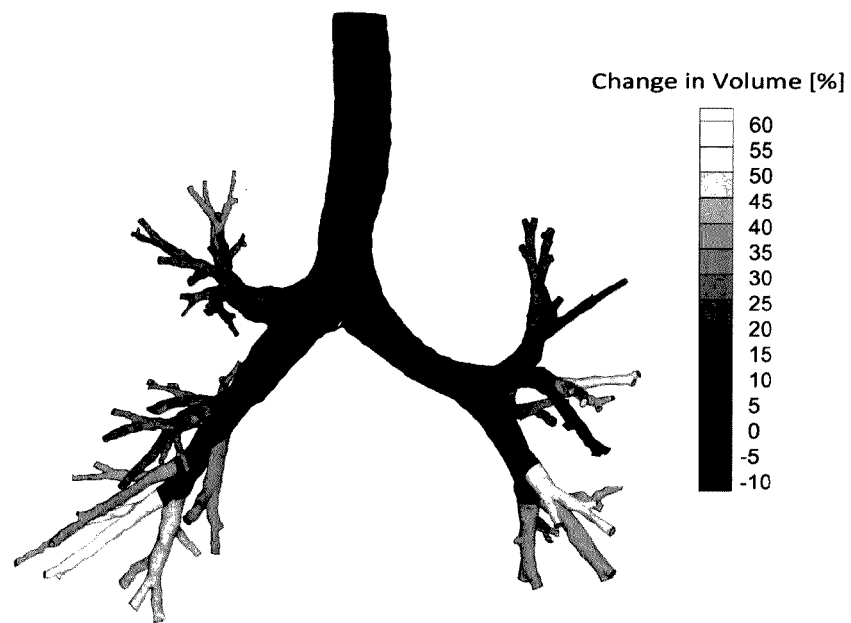
Figure 7B:
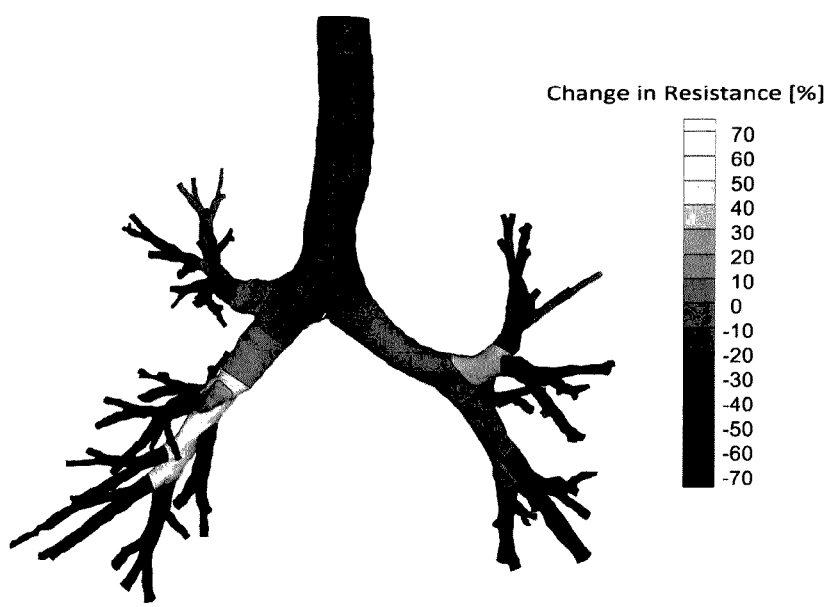

FIG. 7A-B: Changes in airway volume, FIG. 7A, and resistance, FIG. 7B, induced by an intervention determined using functional respiratory imaging.

FIG. 8A-D: Differences in aerosol deposition in upper airways, FIGS. 8A and 8B, and subsequent effective lung dose for two different devices, FIGS. 8C and 8D.

FIG. 9A-E: Stable FEV1 measurement in CF patients over 2 years, FIG. 9A, and significant decline in FRI, FIG. 9B-E, for the same patient indication the insensitive nature of FEV1 and the advantages of the current invention.

FIG. 10A-D: Qualitative, FIG. 10A-C, and quantitative, FIG. 10D, information about the lobar volumes (FRI parameter a) at inspiration (TLC) demonstrating the differences between healthy, COPD and IPF compared to predicted values.

FIG. 11A-D: Qualitative, FIG. 10A-C, and quantitative, FIG. 10D, information about the lobar volumes (FRI parameter a) at expiration (FRC) demonstrating the differences between healthy, COPD and IPF compared to predicted values.

FIG. 12: Qualitative assessment of redistribution of incoming air based on lobar expansion induced by the lung diseases.

FIG. 13A-C: Differences in specific image-based airway volumes (siVaw), specific image based airway radius (siraw) and specific image-based resistance (siRaw), demonstrating the differences between healthy, COPD and IPF.

FIG. 14: Inhalation profiles for healthy, COPD and IPF patients demonstrating the decline in inhalation profile due to COPD and the short deep inhalation profile observed in IPF.

Figure 15:
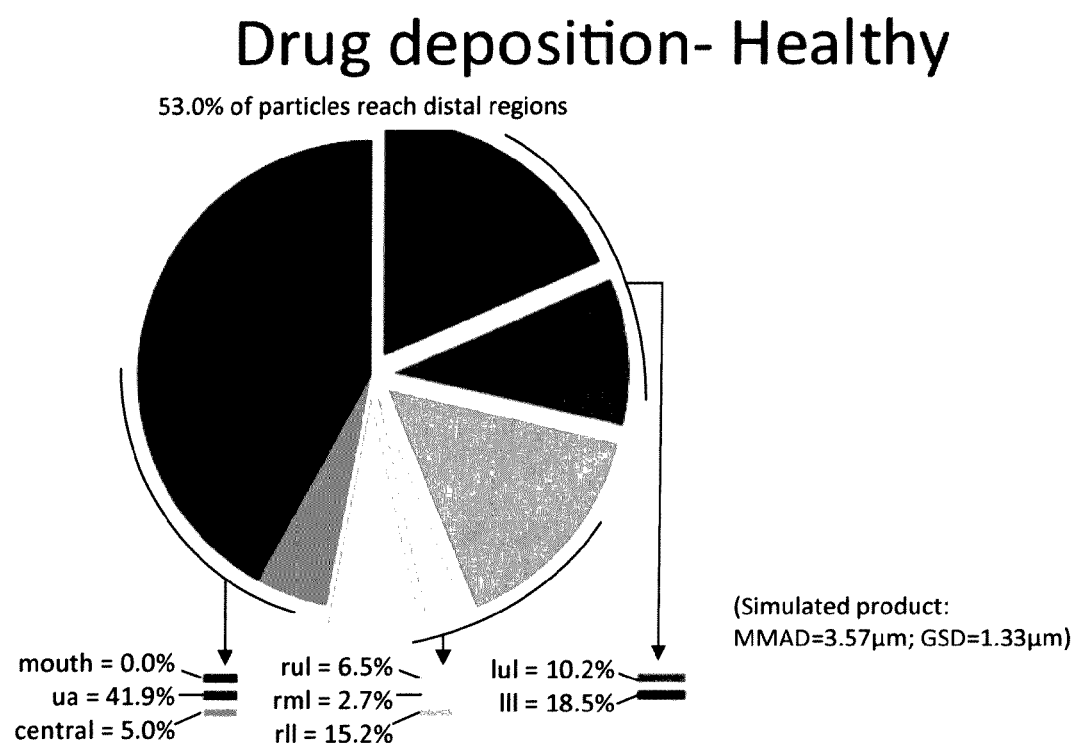

FIG. 15: Resulting drug deposition in healthy subject in mouth, upper airway (UA), central, right upper lobe (rul), right middle lobe (rml), right lower lobe Op, left upper lobe (lul) and left lower lobe (lll).

Figure 16:
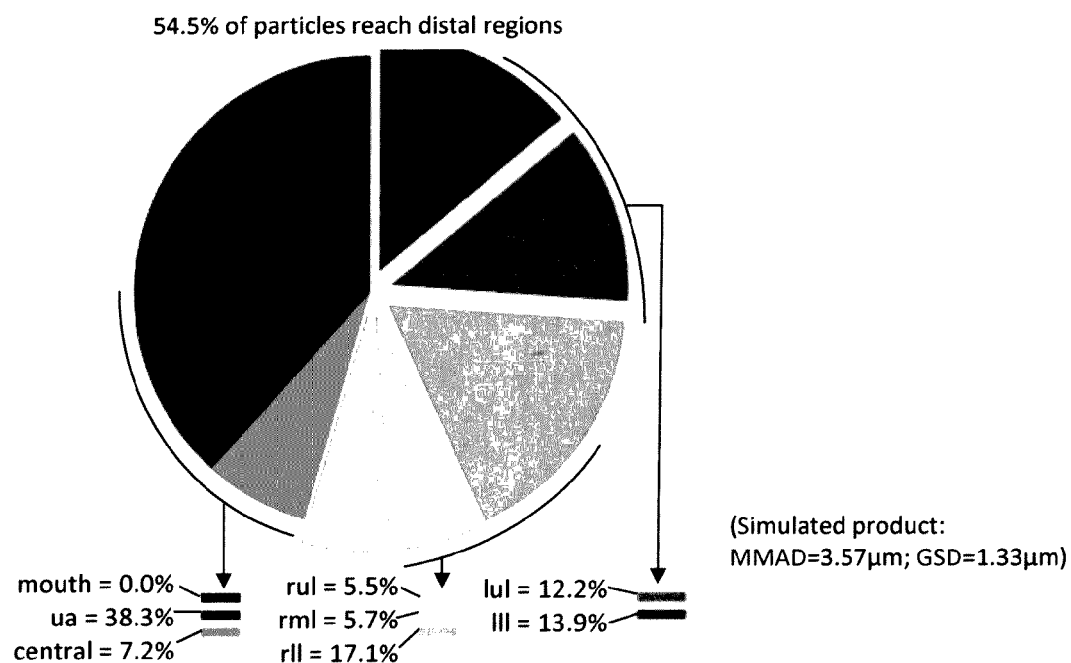

FIG. 16: Resulting drug deposition in COPD patient in mouth, upper airway (UA), central, right upper lobe (rul), right middle lobe (rml), right lower lobe Op, left upper lobe (lul) and left lower lobe (lll).

Figure 17:
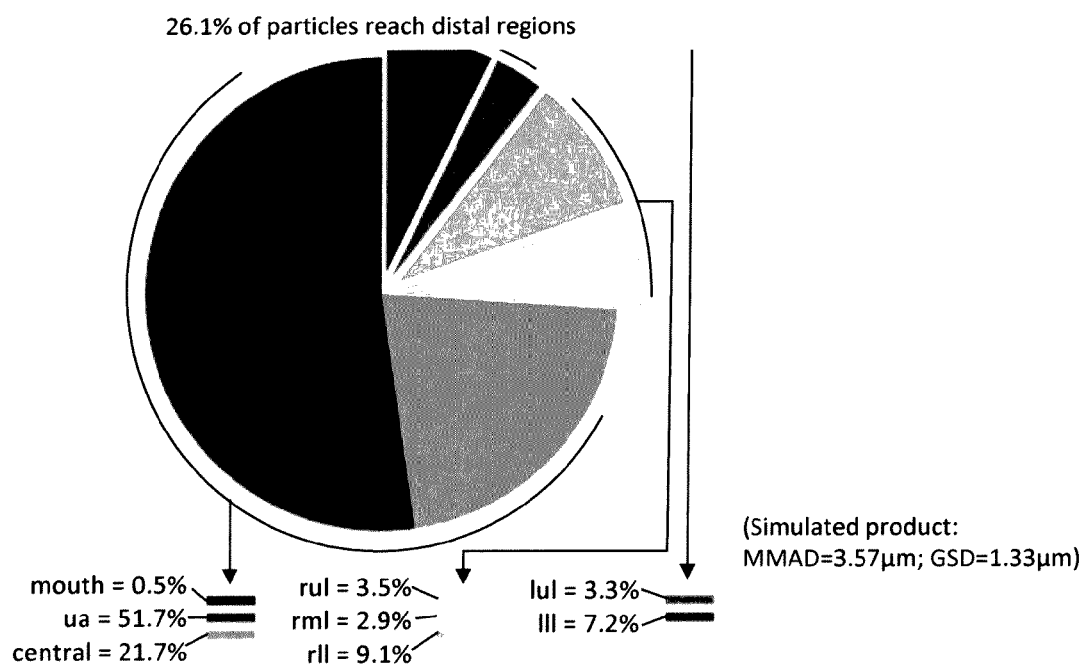

FIG. 17: Resulting drug deposition in IPF patient in mouth, upper airway (UA), central, right upper lobe (rul), right middle lobe (rml), right lower lobe Op, left upper lobe (lul) and left lower lobe (lll).

Figure 18:
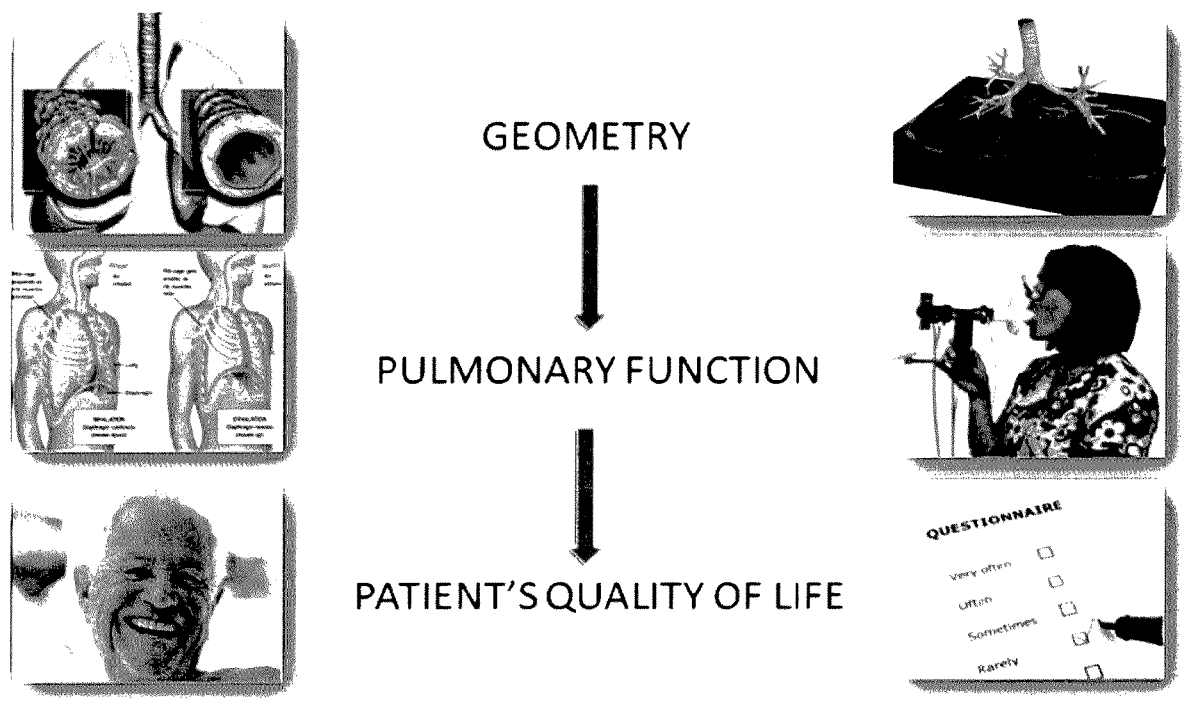

FIG. 18: Various levels that may be relevant for clinical trials, from mode of action to clinical benefit.

Figure 19A:
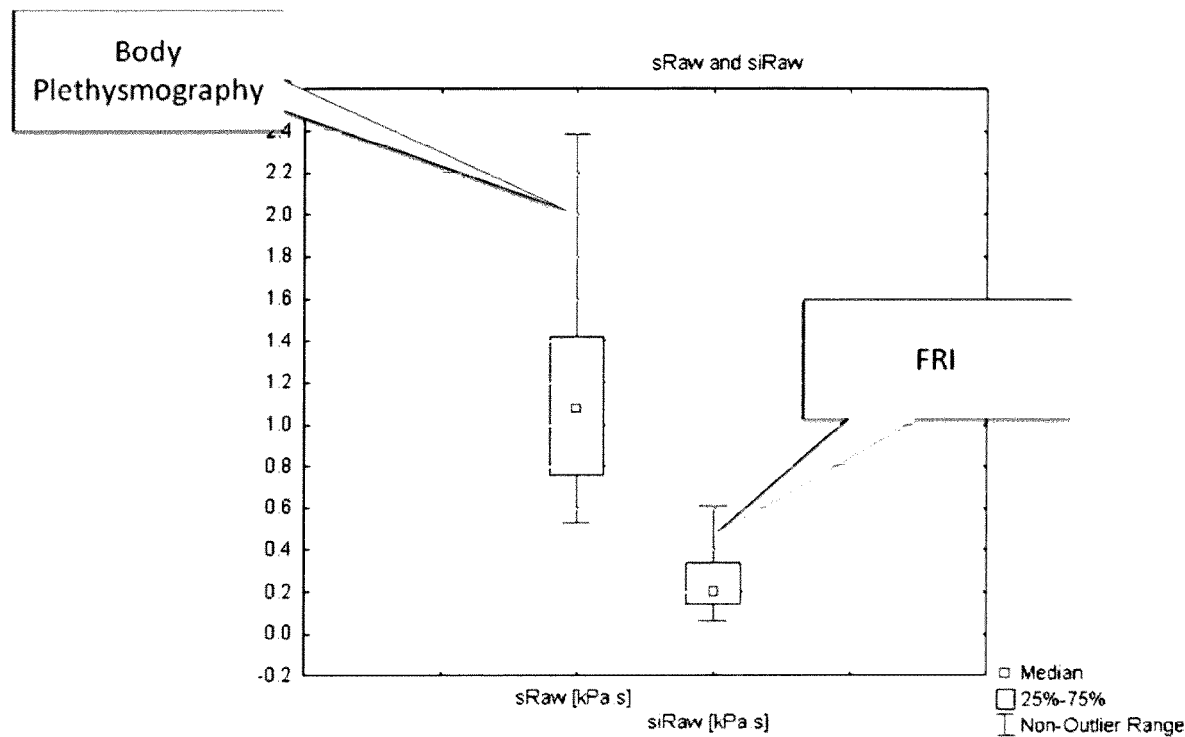
Figure 19B:
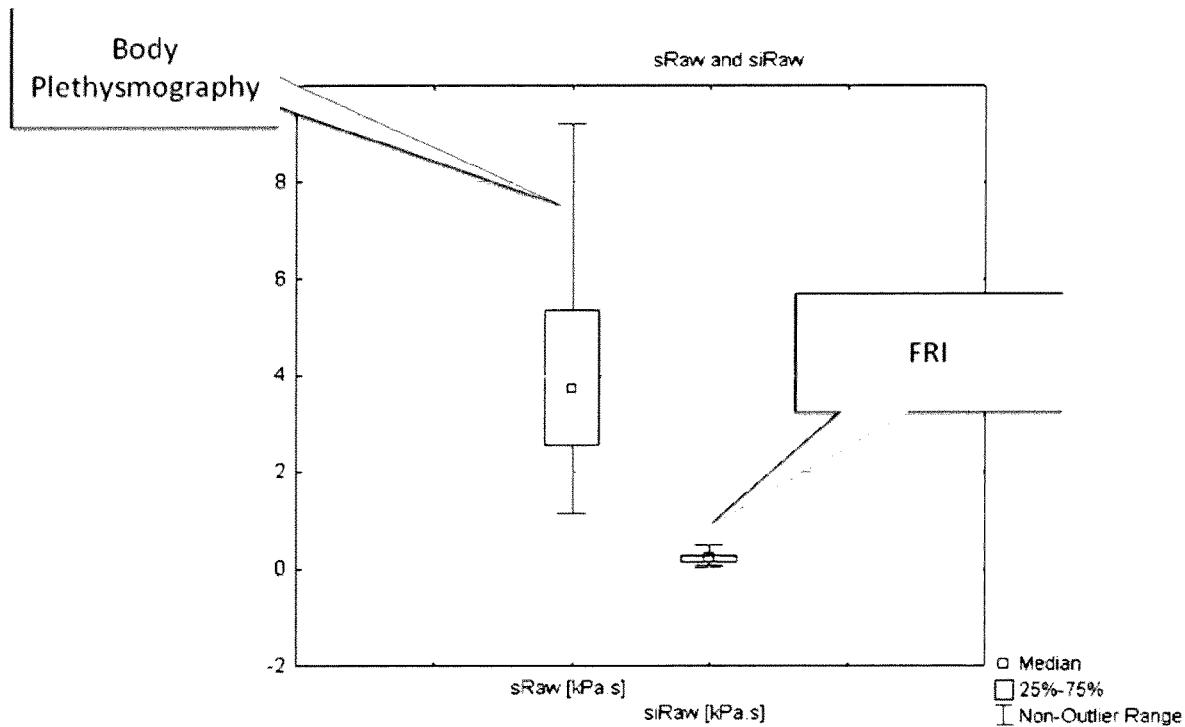

FIG. 19A-B: Signal-to-noise ratio for FRI compared to conventional methods, for an asthma population (FIG. 19A) and a COPD population (FIG. 19B).

Figure 20A:
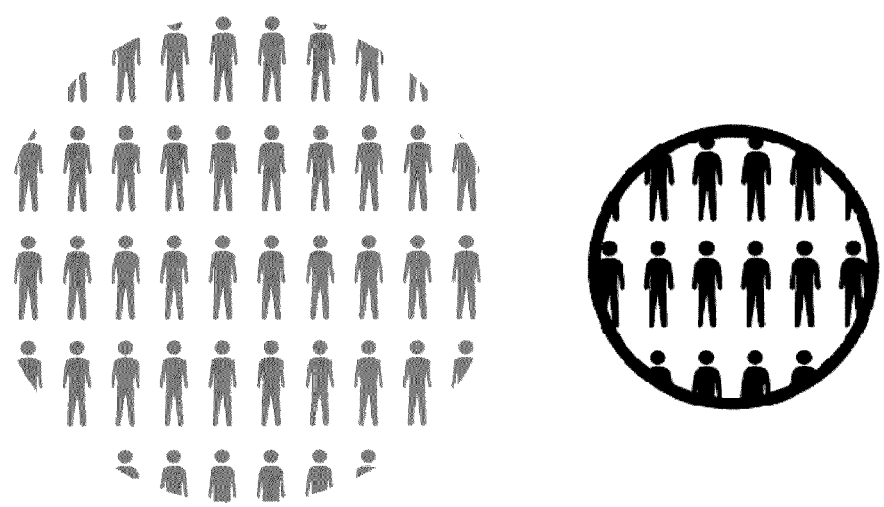
Figure 20B:
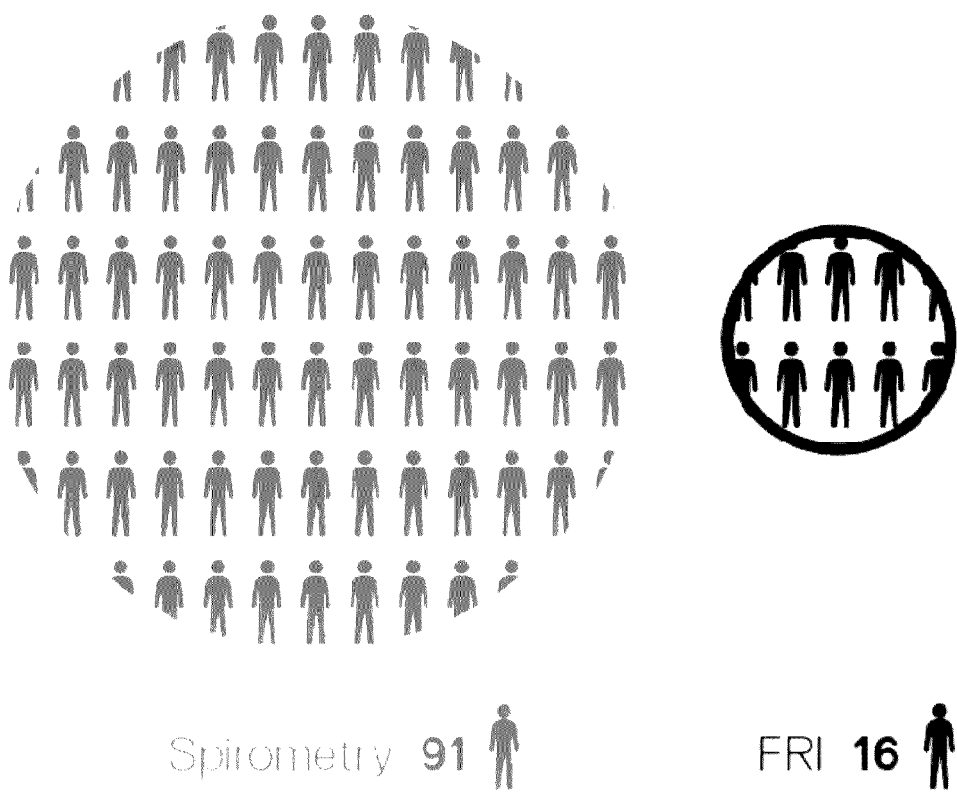

FIG. 20A-B: Required sample size for FRI compared to conventional methods, for an asthma population (FIG. 20A) and a COPD population (FIG. 20B).

Figure 21:
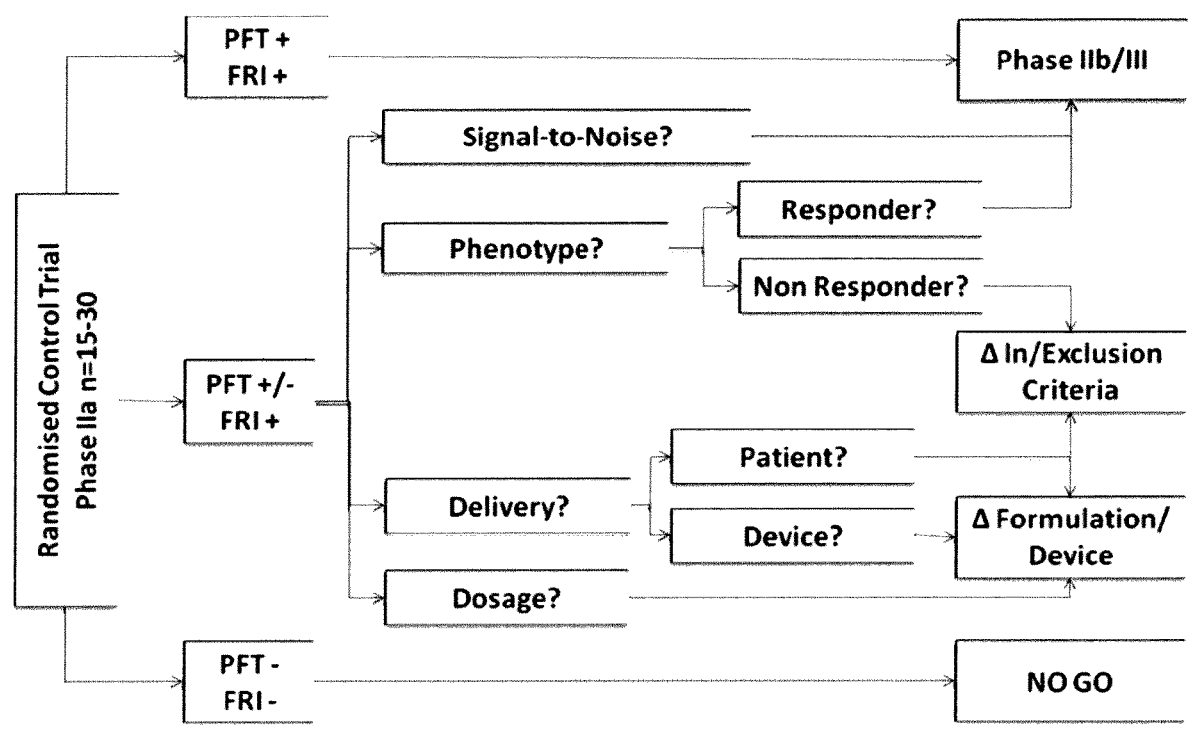

FIG. 21: decision tree for phase IIb or phase III clinical trials.

Figure 22:
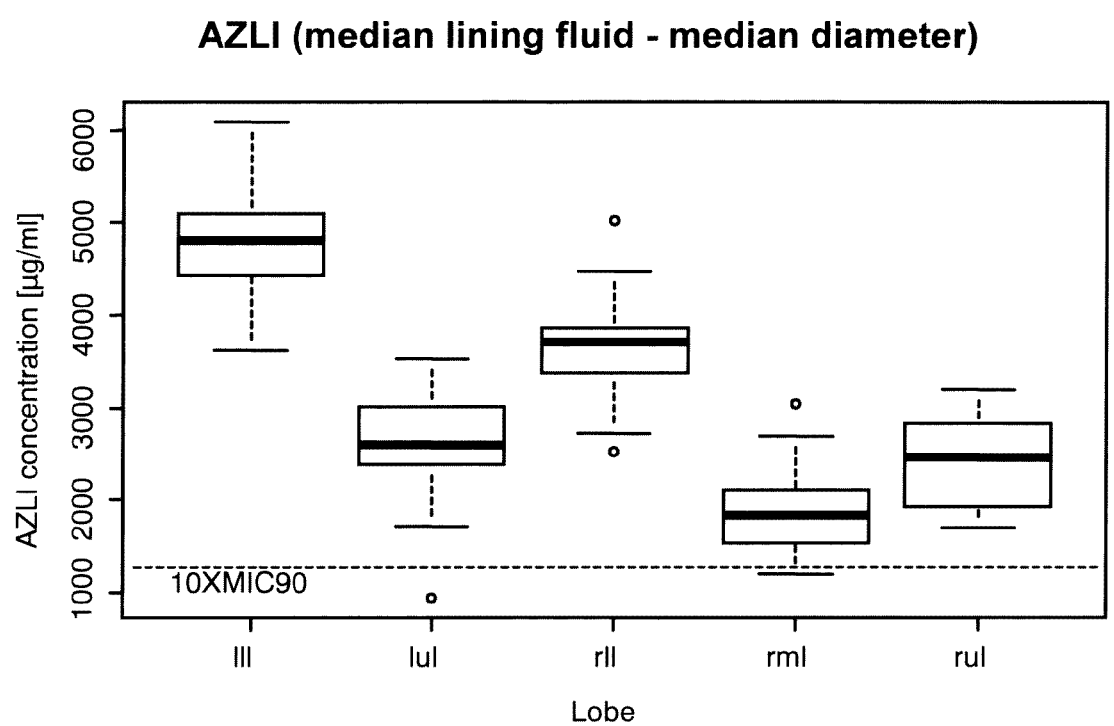

FIG. 22: Distribution of aztreonam lysine (AZLI) in lobar regions of the lung as determined according to the invention.

Figure 23A:
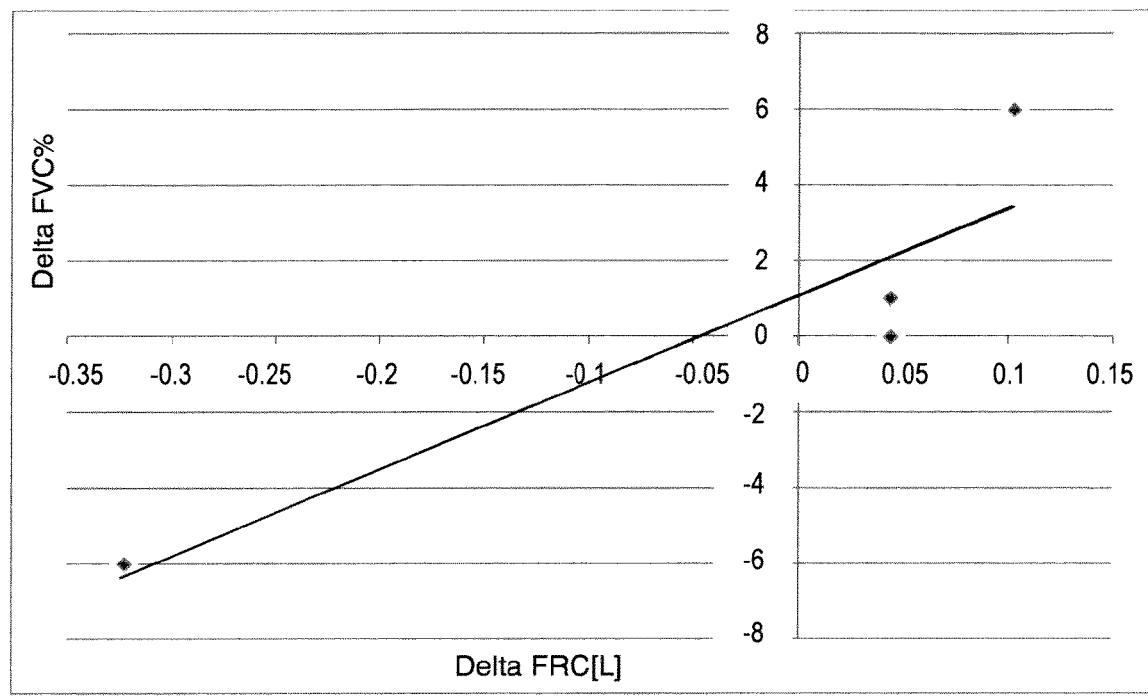
Figure 23B:
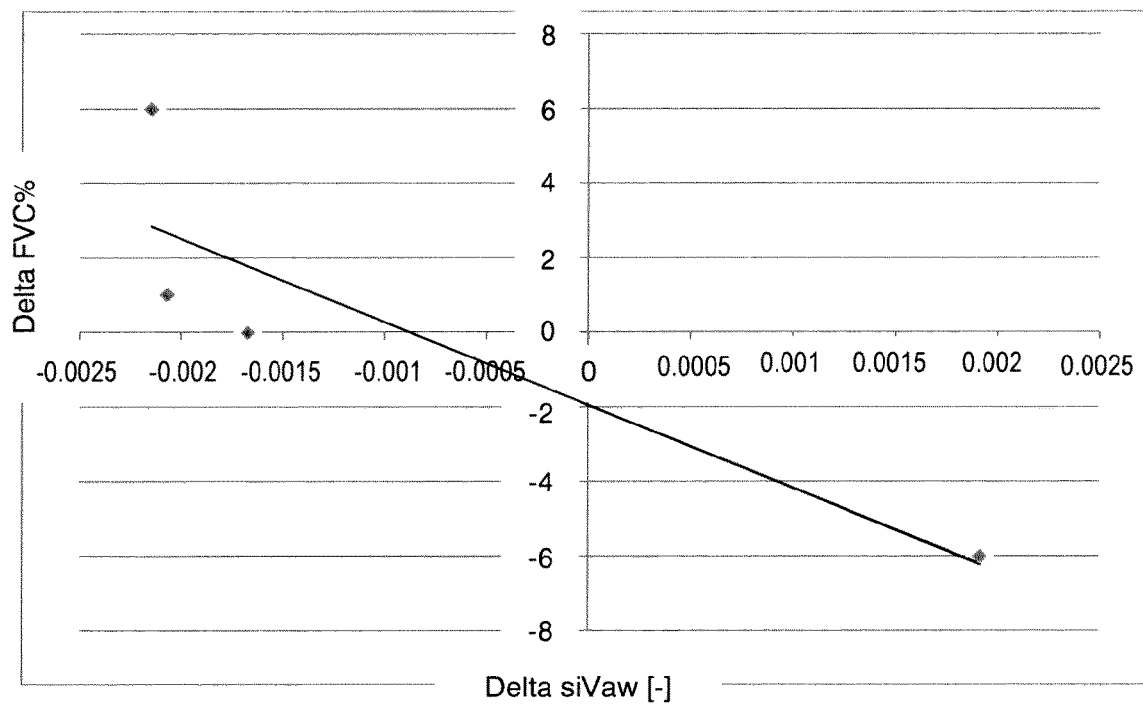
Figure 23C:
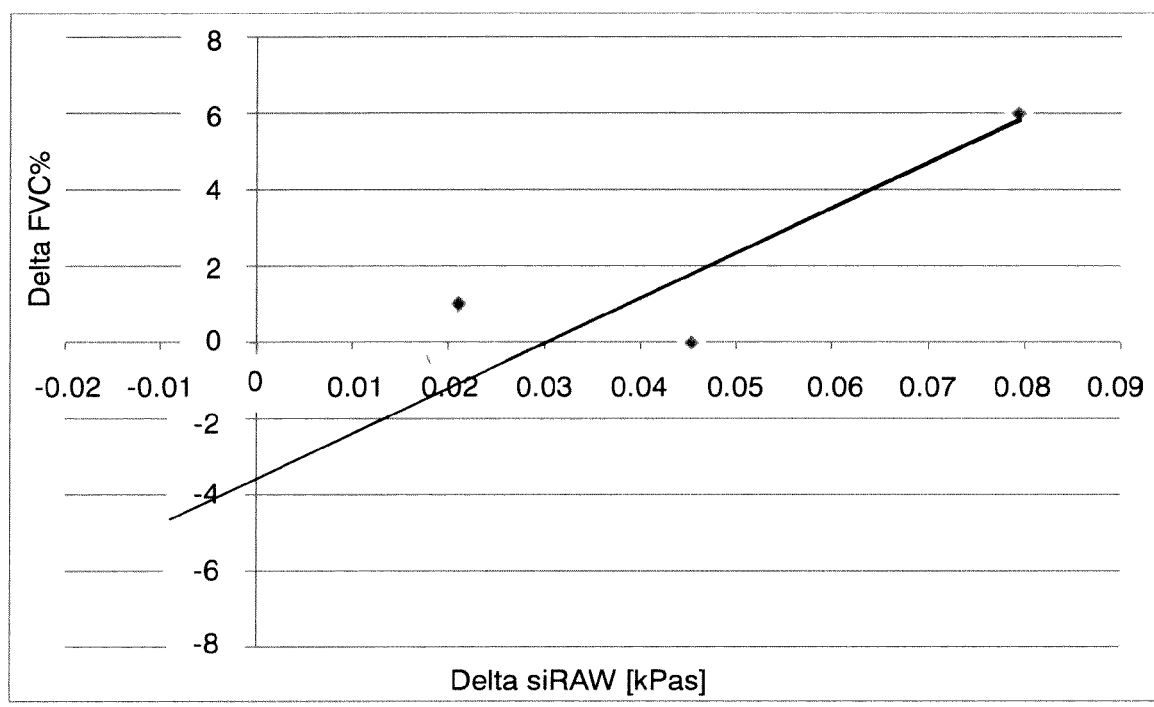
Figure 25:
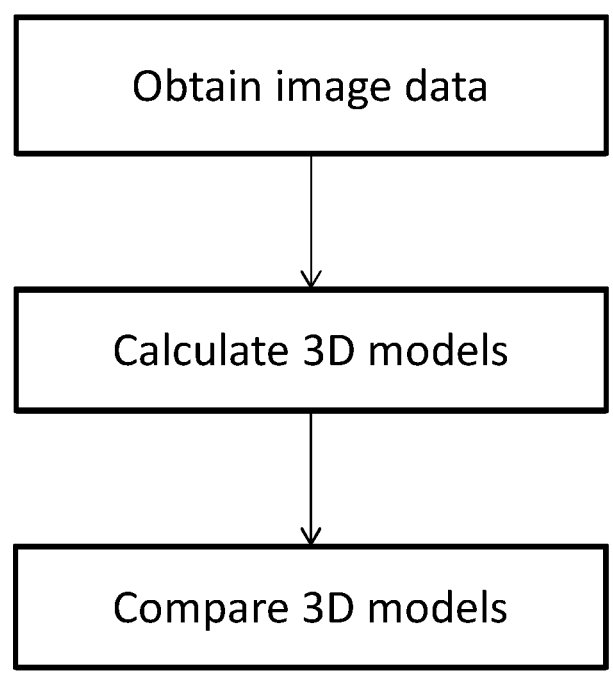

FIG. 23A-C: Graphs showing correlation between disease progression (measured using FVC) and changes in lobar volume (FIG. 23A), airway volume (FIG. 23B), and airway resistance (FIG. 23C).

FIG. 24: Table of data showing the effect of bronchodilation on airway volume (iVaw) and airway wall thickness (iVaww) in asthamatic patients.

DETAILED DESCRIPTION OF THE INVENTION

Before the present methods of the invention are described, it is to be understood that this invention is not limited to particular methods or combinations described, since such methods and combinations may, of course, vary. It is also to be understood that the terminology used herein is not intended to be limiting, since the scope of the present invention will be limited only by the appended claims.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of".

The recitation of numerical ranges by endpoints includes all numbers and fractions subsumed within the respective ranges, as well as the recited endpoints.

Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any$\geq 3$, $\geq 4$, $\geq 5$, $\geq 6$ or $\geq 7$ etc. of said members, and up to all said members.

All references cited in the present specification are hereby incorporated by reference in their entirety. In particular, the teachings of all references herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

In the present description of the invention, reference is made to the accompanying drawings that form a part hereof, and in which are shown by way of illustration only of specific embodiments in which the invention may be practiced. It is to be understood that other embodiments may be utilized and structural or logical changes may be made without departing from the scope of the present invention. The following detailed description, therefore, is not to be taken in a limiting sense, and the scope of the present invention is defined by the appended claims.

The present invention concerns a method for determining a respiratory condition in a subject. The present invention also concerns a method for assessing the efficacy of a treatment of a respiratory condition. The present invention also concerns a method for optimizing a treatment protocol of a respiratory condition. Preferably, the present invention concerns a method for processing data to achieve the above goals. The method according to the invention will herein also be referred to as "functional respiratory imaging" or FRI. The "respiratory system" refers to the intra- and extra-thoracic airways and the lungs.

The method according to the invention comprises the steps of:
a) obtaining image data concerning two or more three-dimensional images of the subject's respiratory system, which images have been previously acquired during an assessment period;
b) calculating a specific three-dimensional structural model of the subject's respiratory system from each of the data obtained in step a);
c) comparing the three-dimensional structural models of the subject's respiratory system for each of the image data obtained in step a) to determine a respiratory condition, or to assess the efficacy of a treatment for a respiratory condition, or to optimize a treatment protocol for a respiratory condition. In other words, the method comprises the steps of:
a) obtaining image data concerning two or more three-dimensional images of the subject's respiratory system, which images have been previously acquired during an assessment period;
b) calculating a specific three-dimensional structural model of the subject's respiratory system for each of the two or more three-dimensional images of step a);
c) comparing the three-dimensional structural models of step b) with each other to determine a respiratory condition or to assess the efficacy of a treatment for a respiratory condition or to optimize a treatment protocol for a respiratory condition.

In an embodiment, the method is used for determining a respiratory condition. In an embodiment, the method is used for assessing the efficacy of a treatment of a respiratory condition. In an embodiment, the method is used for optimizing a treatment protocol of a respiratory condition. In an embodiment, the method is used for a combination of the above-mentioned purposes.

The images, or image data, of step a) have been previously acquired during an assessment period. The images may have been previously acquired using any method of the art. Such methods include magnetic resonance imaging (MRI), positron emission tomography (PET) and computer tomography (CT) imaging to name a few. In a preferred embodiment, the image data of step a) were previously acquired using a computed tomography (CT) or a magnetic resonance imaging (MRI) scan, preferably using a CT scan, preferably using a high-resolution CT (HRCT) scan, or a micro CT scan (in particular if used on an animal subject). HRCT scans can then be converted into patient-specific 3D computer models. From the image data, a three-dimensional structural model of the subject's lung may be generated. The structural model refers to an internal structural model, especially indicating tissue structures. Preferably, the images are acquired at two lung volumes; one at total lung capacity (TLC), the lung level attained after a deep inhalation, and one at functional residual capacity (FRC), the lung level after normal expiration. The subject may be a human or an animal.

The assessment period may have provided image data over a certain time period, for example seconds, minutes, days, weeks, months or years. In a preferred embodiment, the assessment period has provided image data in pre- and post-treatment stages. When the invention is applied to determining efficacy of treatment, image data and structural models of the lung may be obtained prior to and after the start of treatment (e.g. at a 1, 2, 3, 4, 5, 6, 7, 8, 9, 10, 11, 12 months intervals just prior to treatment, and/or at regular 1, 2, 3, 4, 5, 6, 7, 8, 9, 10, 11, 12 month intervals after treatment, and/or at regular 1, 2, 3, 4, 5, 6, 7, 8, 9, 10, 11, 12 month intervals during treatment). Also, smaller time periods, for example ranging from 15 min to a few hours, are suitable according to the invention. In a preferred embodiment, the assessment period has provided image data over a breathing cycle of the subject, preferably at functional residual capacity (FRC) and total lung capacity (TLC). As used herein, the terms "expiration" or "exhalation" will refer to functional residual capacity (FRC), and the terms "inspiration" or "inhalation" will refer to total lung capacity (TLC). In a preferred embodiment, the image data of step a) comprise CT images at FRC and TLC, preferably high-resolution CT images at FRC and inspiration TLC. In some preferred embodiments, the assessment period comprises a breathing cycle and the image data of step a) comprise computer tomography, CT, images at functional residual capacity, FRC, and at total lung capacity, TLC, preferably high-resolution CT images at FRC and TLC. In some preferred embodiments, the assessment period comprises pre- and post-treatment stages and the image data of step a) comprise pre- and post-treatment images, preferably high-resolution pre- and post-treatment CT images.

In a preferred embodiment, the structural model of step b) is calculated using segmentation principles. During the segmentation procedure, voxels (volume elements) of the same anatomical structure of interest are placed in a separate mask. This mask is used to reconstruct the airways in three dimensions. The segmentation principle is known in the art, and described, for example, in "*Flow analyses in the lower airways: patient-specific model and boundary conditions* De Backer J W, Vos W G, Gorlé C D, Germonpré P, Partoens B, Wuyts F L, Parizel P M, De Backer W. *Med Eng Phys*. 2008 September; 30(7):872-879"; which is hereby incorporated in its entirety by reference.

In a preferred embodiment, high resolution computed tomography images are used to create patient specific three-dimensional representations of the lungs, the lung lobes, the airways, the blood vessels, the airway walls and the emphysematous regions.

The method preferably starts by acquiring high-resolution CT images at expiration and inspiration. Anatomical structures are subsequently identified by selection regions consisting of similar densities represented by the Hounsfield unit range in the scans. The Hounsfield unit is a unit used in medical imaging (MSCT) to describe the amount of x-ray attenuation of each "voxel" in the 3D image. The voxels are normally represented as 12-bit binary numbers, and therefore have 212=4096 possible values. These values can be arranged on a scale from −1024 HU to +3071 HU, calibrated so that −1024 HU is the attenuation produced by air and 0 HU is the attenuation produced by water.

In an embodiment, the specific three-dimensional structural model of the subject's respiratory system comprises a three-dimensional structural model of the subject's lung structure.

In an embodiment, the specific three-dimensional structural model of the subject's respiratory system comprises a three-dimensional structural model of the subject's lobar structure. Using data obtained from the three dimensional lung model, a specific three-dimensional model of the subject's lobar volumes may be constructed i.e. the lobar volumes are segmented based on a previous lung model. Preferably, the structural model of step b) is calculated using lobar segmentation. The right lung has two fissures: the right oblique fissure, and the right horizontal fissure; while the left lung only has one fissure: the left oblique fissure. Consequently, a normal human has five lung lobes, three on the right side: right upper lobe (RUL), right middle lobe (RML), and right lower lobe (RLL); and two on the left side: left upper lobe (LUL) and left lower lobe (LLL). In an embodiment, initially the complete right and left lungs may be segmented, after which the fissure lines may be identified. These lines indicate the division between the several lung lobes, and can be distinguished from the thorax model. These lines may then be converted into cutting planes that subdivide the lungs into their respective lobar volumes. Lobar segmentation may be performed manually or automatically. Preferably, separate lobar volume models are constructed at total lung capacity (TLC), and at functional residual capacity (FRC). By performing the lobar segmentation at FRC and TLC level, it is possible to assess the patient specific mass flow rate towards each lobe. This data may be used as a boundary conditions in subsequent flow simulations i.e. Computational Fluid Dynamics (CFD).

In an embodiment, the specific three-dimensional structural model of the subject's respiratory system comprises a three-dimensional structural model of the subject's airway structure. Where appropriate, separate airway models are constructed at total lung capacity (TLC), and at functional residual capacity (FRC). When the invention is applied to determining efficacy of treatment, separate airway models are constructed from the lung models obtained prior to and after the start of treatment. Preferably, the airway model is generated at TLC, though an airway model generated at FRC may be used at any time when necessary, for instance, when it appears to be more accurate.

In an embodiment, the specific three-dimensional structural model of the subject's respiratory system comprises a three-dimensional structural model of the subject's blood vessel structure.

In an embodiment, the specific three-dimensional structural model of the subject's respiratory system comprises a three-dimensional structural model of the subject's airway wall structure.

In an embodiment, the specific three-dimensional structural model of the subject's respiratory system comprises a three-dimensional structural model of the subject's emphysematous regions.

In a preferred embodiment, step b) comprises the step b') calculating one or more outcome parameters from the specific three-dimensional structural model of the subject's respiratory system; and step c) comprises the step c') comparing the outcome parameters for each of the data obtained in step a) to determine a respiratory condition or to assess the efficacy of a treatment of a respiratory condition or to optimize a treatment protocol for a respiratory condition. The outcome parameter may be selected from a variation of outcome parameters. Non-limiting examples of such outcome parameters include: lobar volume (or patient specific lobar ventilation), airway volume, lobar emphysema, lobar blood vessel volume, airway wall thickness, airway resistance, changes in airway volume and resistance, and aerosol deposition characteristics (or effective lung dose).

In a preferred embodiment, the specific three-dimensional structural model of the subject's respiratory system comprises a three-dimensional structural model of the subject's lobar structure and a three-dimensional structural model of the subject's airway structure, and wherein step b') further comprises the following steps:

b") modeling by a computer, the air flow through the airway, using the three-dimensional structural model of the subject's lobar structure and the three-dimensional structural model of the subject's airway structure; and b'") optionally, modeling by a computer, the structural behavior of the airway and the interaction with the flow, using the three-dimensional structural model of the subject's lobar structure and the three-dimensional structural model of the subject's airway structure. Preferably, the modeling of step b") comprises computational fluid dynamics (CFD), comprising solving the Navier-Stokes equations numerically. CFD can simulate the flow behavior in the specific three-dimensional airway structure model by solving the mathematical flow equations (Navier-Stokes equations) numerically: "De Backer J W, Vanderveken O M, Vos W G, Devolder A, Verhulst S L, Verbraecken J A, Parizel P M, Braem M J, Van de Heyning P H and De Backer W A. *Functional imaging using computational fluid dynamics to predict treatment success of mandibular advancement devices in sleep-disordered breathing J Biomech* 40: 3708-3714, 2007", "De Backer J W, Vos W G, Devolder A, Verhulst S L, Germonpre P, Wuyts F L, Parizel P M and De B W. *Computational fluid dynamics can detect changes in airway resistance in asthmatics after acute bronchodilation, J Biomech* 41: 106-113, 2008", and "De Backer J W, Vos W G, Verhulst S L and De B W. *Novel imaging techniques using computer methods for the evaluation of the upper airway in patients with sleep-disordered breathing: a comprehensive review. Sleep Med Rev* 12: 437-447, 2008", which are hereby incorporated by reference in their entirety. Also the subsequent structural behavior of the respiratory system, the interaction with the flow and the remodeling may be determined using a combination of CFD and FEA techniques. The structural behavior of the model may be determined by solving the structural equations for stresses, stains, displacements etc. as explained the biomedical engineering handbook (The Biomedical Engineering Handbook by Joseph Bronzino, IEEE press). This analysis allows, for example, for an assessment of the change in airway geometry due to the pressure exerted on the walls. In performing CFD, the three-dimensional structure model may be subdivided into a plurality of discrete elements. The collection of these elements is called a computational mesh or grid. In each of the grid nodes, the flow equations are solved. Preferably the airway model constructed at TLC is used, however, the FRC model can be used at any time when necessary, for example, when it appears to be more accurate. Preferably, the three-dimensional structural model of the subject's lobar structure is used to determine boundary conditions for the computational fluid dynamics. With a large system such as a lung, solution of the flow equations may be assisted by determining adequate boundary conditions to close the system of equations, which boundary conditions are preferably determined using the specific three-dimensional model of the subject's lobar volumes as mentioned above. Boundary conditions can be derived from the CT images by assessing the lobar expansion from FRC to TLC. This indicates the fraction of the inhaled air that goes to each lobe for that specific patient. To make the models as accurate as possible, this patient-specific information may be reflected in the flow simulations. In practice, this may be achieved by adjusting the pressures at the bronchioli outlets to such an extent that the model mass flow rate is identical to the mass flow rate obtained via CT images.

For example, in a preferred embodiment of the invention:
the specific three-dimensional structural model of the subject's respiratory system further comprises a three-dimensional structural model of the subject's lung structure at TLC and FRC; and the specific three-dimensional structural model of the subject's respiratory system comprises a three-dimensional structural model of the subject's lobar structure at TLC and FRC;

wherein this specific three-dimensional structural model of the subject's respiratory system is used to determine mass flow rate towards each lobe, and subsequently to obtain the boundary conditions for said computational fluid dynamics.

In an embodiment, the outcome parameter is the lobar volume, herein also referred to as "parameter a". The assessment of lobar volumes yields how much air is present in the individual lobes. Lobar volumes are obtained by first determining the lung volume of the right and left lung respectively and the fissure lines. Preferably the lobar volume is measured at FRC and TLC. The differential between the lobar volumes at expiration and inspiration is a measure of the amount of air reaching the individual lobes and hence provides patient specific lobar ventilation, which can also be used as an outcome parameter. FIG. 1 illustrates lobar volumes at expiration (FRC), FIG. 1A, and inspiration (TLC), FIG. 1B.

In an embodiment, the outcome parameter is the airway volume, herein also referred to as "parameter b". Preferably, the airway volume is measured at FRC and TLC. In an embodiment, the voxels that make up the airway lumen are determined, showing the region where the air passes through and where the inhaled air experiences resistance. The patient specific airways can be reconstructed up to the level of the small airways after which the resolution of the scan may be insufficient to further distinguish between intraluminal and alveolar air. The assessment of the inspiratory and expiratory airway geometry allows for the detection of airway closure and subsequent airway trapping. Individual airway diameters, lengths and volume may be determined. The airway length or airway diameter can also be used as an outcome parameter. FIG. 2 illustrates airway segmentation at expiration, FIGS. 2A and 2B, and inspiration, FIGS. 2C and 2D.

In an embodiment, the outcome parameter is lobar emphysema, herein also referred to as "parameter c". Assessment of the interconnectivity of voxels with a Hounsfield unit range of air allows for the determination of emphysema on a lobar level. Emphysema is the destruction of lung tissue, often caused by noxious agents such as cigarette smoke or environmental pollution. Destruction of tissue results in a reduction of local perfusion (blood flow), thereby potentially causing a ventilation (air)-perfusion (blood) mismatch. FIG. 3 illustrates the assessment of emphysematous regions on lobar level through the analysis of air voxel interconnectivity. FIG. 3A shows the identification of emphysema in the CT images, while FIG. 3B shows the extent of emphysema in a 3D fashion and on a lobar level. FIG. 3B shows the difference between a normal subject and a subject suffering from Chronic Obstructive Pulmonary Disease (CPOD).

In an embodiment, the outcome parameter is the lobar blood vessel volume, herein also referred to as "parameter d". Similar compared to the segmentation approach used to determine airway volumes, as described above, the same approach (grouping voxels consisting of a predefined Hounsfield unit range) can be used to assess the volume of blood vessels in individual lobes. The percentage blood vessel in a lobe could be considered a measure of lobar perfusion and hence can be used to assess ventilation perfusion matching. FIG. 4 illustrates lobar blood vessel segmentation.

In an embodiment, the outcome parameter is the airway wall thickness, herein also referred to as "parameter e".

Using the definition of the segmented airway volumes, it becomes possible to obtain definitions of the airway wall. By dilating the segmented mask restricted to the Hounsfield unit range of the tissue, the airway wall can be selected and measured. Over time, changes in airway wall thickness could indicate changes in inflammatory disease processes. FIG. 5 illustrates airway wall thickness assessment.

In an embodiment, the outcome parameter is the airway resistance, herein also referred to as "parameter f". Preferably, the airway resistance is measured at FRC and TLC. Computational fluid dynamics measurements using boundary conditions, for example extracted from the high resolution CT images (i.e. lobar expansion), may be used to determine local resistance parameters on lobar level. The majority of the resistance may be captured via the patient specific morphology of the central and distal airways. The peripheral airways can be taken into account using the CT-based lobar boundary conditions, as described above. FIG. 6 illustrates an assessment of airway resistance using computational fluid dynamics and patient specific boundary conditions.

In an embodiment, the outcome parameter is the airway volume and/or resistance, herein also referred to as "parameter g". Many interventions in the respiratory field are aimed at changing the airway volumes and resistance. The method according to the invention can be used to assess on a lobar and segmental level the changes in airway volumes and resistances by overlaying multiple measurements and comparing the outcome parameters. FIG. 7 illustrates changes in airway volume, FIG. 7A, and resistance, FIG. 7B, induced by an intervention determined using functional respiratory imaging.

In an embodiment, the outcome parameter is related to aerosol deposition characteristics, such as the effective lung dose, herein also referred to as "parameter h". An important measure in inhalation therapy is the effective lung dose. The method according to the invention can determine the patient specific lung dose as a function of the patient specific morphology, aerosol and device characteristics, and inhalation profiles. FIG. 8 illustrates differences in aerosol deposition in upper airways, FIGS. 8A and 8B, and subsequent effective lung dose for two different devices, FIGS. 8C and 8D. The lung deposition was increased by 9%.

The respiratory condition may be selected from a variation of respiratory conditions. These conditions may be any that result in reduced gaseous exchange. Non-limiting examples of such respiratory conditions include: lung transplantation, radiotherapy, cystic fibrosis (CF), idiopathic pulmonary fibrosis (IPF), chronic obstructive pulmonary disease (COPD), and asthma. Other suitable conditions comprise diseases which manifest as a result of other restrictive disorders, such as neuromuscular disorders that might include amyotrophic lateral sclerosis (ALS), myotonic dystrophy (Steinert's disease), Duchenne muscular dystrophy, Acid maltase deficiency, and Emery-Dreifuss myopathy. In some preferred embodiments, the respiratory disease is an orphan disease. An orphan disease is a rare disease that affects a small percentage of the population. Such diseases include cystic fibrosis, idiopathic pulmonary fibrosis, sarcoidosis, pulmonary alveolar proteinosis, and alpha 1 antitrypsin deficiency.

In a preferred embodiment, the respiratory condition is related to a lung transplantation. Lung transplantations are considered for patients suffering from extreme emphysema, cystic fibrosis or idiopathic conditions such as idiopathic pulmonary fibrosis. The process of a lung transplantation is extremely challenging, as there is often very little time between identification of the donor and the transplant itself. Unfortunately the donor pool is limited and a high rejection rate, up to 50%, occurs after transplantation.

In a preferred embodiment, the method according to the invention comprises geometrical matching of donor/receptor. One of the factors that can reduce the chance of rejection is the accurate geometrical matching of the donor with the receptor. If the geometry and the function (in terms of resistance) are similar between the donor and receptor, the receptor's immune system will be less activated, thereby reducing the chances of rejection. The outcome parameters according to the invention can be used to accurately describe both the receptor as well as the donor. The parameters that are of most importance are parameters a, b and/or f, as described above. In an embodiment, the method according to the invention comprises geometrical matching of donor/receptor using outcome parameter a. In an embodiment, the method according to the invention comprises geometrical matching of donor/receptor using outcome parameter b. In an embodiment, the method according to the invention comprises geometrical matching of donor/receptor using outcome parameter f.

In a preferred embodiment, the method comprises detection of bronchiolitis obliterans (BOS), preferably early detection of BOS. Bronchiolitis obliterans is a lung condition preceding rejection of transplanted lungs. Today it remains challenging to detect the occurrence of BOS as spirometry lacks the sensitivity to detect subtle changes in lung geometry and function. Biopsies could indicate the onset of inflammation but are invasive and limited to a very select number of biopsy locations. The method according to the invention can be used to detect subtle changes in respiratory geometry and function by assessing the airway resistance, volumes, airway wall thickness, local perfusion and/or stiffness. The outcome parameters of main interest in this respect are outcome parameters a, b, d, e, f, and/or g, as described above. In an embodiment, the method according to the invention comprises detection of bronchiolitis obliterans (BOS) using outcome parameter a. In an embodiment, the method according to the invention comprises detection of bronchiolitis obliterans (BOS) using outcome parameter b. In an embodiment, the method according to the invention comprises detection of bronchiolitis obliterans (BOS) using outcome parameter d. In an embodiment, the method according to the invention comprises detection of bronchiolitis obliterans (BOS) using outcome parameter e. In an embodiment, the method according to the invention comprises detection of bronchiolitis obliterans (BOS) using outcome parameter f. In an embodiment, the method according to the invention comprises detection of bronchiolitis obliterans (BOS) using outcome parameter g.

In a preferred embodiment, the method comprises optimization of an inhalation treatment. To avoid lung rejection in case of BOS, inhalation medication (usually inhaled corticosteroids) can be administered. However the local lung dose and the site of deposition are important to maximize the effect of the treatment. Outcome parameter h can assist in determining the correct dose, inhalation profile and/or device/formulation to use in order to optimize the treatment in a patient specific fashion. In an embodiment, the method comprises optimization of an inhalation treatment using outcome parameter h.

In a preferred embodiment, the respiratory condition is related to radiotherapy. Radiotherapy is an intervention used to treat patients suffering from lung cancer. The carcinomatous tissue is radiated to destroy the cancer cells and prevent the tumor from growing. A side effect of ionizing radiation is the potential to radiation induced lung injury, consisting of inflammation (radiation pneumonitis) and in a later phase lung scarring (fibrosis). Both conditions could be lethal and require early detection to start treatment to avoid cascading of severe adverse events.

In an embodiment, the method comprises detection of radiation pneumonitis and/or fibrosis. Outcome parameters according to the invention can be used to detect early signs of radiation induced lung injury. Parameters such as airway volume (parameters b or g), airway wall thickness (parameter e) and resistance (parameters f or g) can indicate the onset of inflammation. Lobar expansion (parameter a) and internal airflow distribution (parameter f) can detect the onset of fibrosis or stiffening of the lungs. In an embodiment, the method comprises detection of radiation pneumonitis and/or fibrosis using outcome parameter a. In an embodiment, the method comprises detection of radiation pneumonitis and/or fibrosis using outcome parameter b. In an embodiment, the method comprises detection of radiation pneumonitis and/or fibrosis using outcome parameter e. In an embodiment, the method comprises detection of radiation pneumonitis and/or fibrosis using outcome parameter f. In an embodiment, the method comprises detection of radiation pneumonitis and/or fibrosis using outcome parameter g.

In an embodiment, the method comprises optimization of an inhalation treatment. To reduce the inflammation and the resulting fibrosis, patients are often treated using inhalation medication. Similar to the cases as described above, it is important to tailor the inhalation treatment to the specific patient to ensure the target regions are effectively reached. Outcome parameter h can assist in determining the correct dose, inhalation profile and/or device/formulation to use in order to optimize the treatment in a patient specific fashion. In an embodiment, the method comprises optimization of an inhalation treatment using outcome parameter h.

In a preferred embodiment, the respiratory condition is related to cystic fibrosis. Cystic fibrosis is a disease caused by a defective gene, which causes thick mucus, thereby severely impairing the respiratory function. There is no cure for the disease at this stage and the patients become progressively worse. Despite the fact that no cure exists, it is crucially important to be able to detect early decline in lung function.

In a preferred embodiment, the method comprises optimization of an inhalation treatment for cystic fibrosis; typically treatment comprises inhalation medication (usually inhaled antibiotic such as aztreonam lysine (AZLI) can be administered. However the local lung dose and the site of deposition are important to maximize the effect of the treatment. Outcome parameter h (aerosol deposition characteristics) can assist in determining the correct dose, inhalation profile and/or device/formulation to use in order to optimize the treatment in a patient specific fashion. In an embodiment, the method comprises optimization of an inhalation treatment for cystic fibrosis using outcome parameter h. AZLI deposition was simulated using patient specific geometries and patient specific inhalation profiles. Local deposition characteristics of inhaled Aztreonam lysine (AZLI) were simulated using Functional Respiratory Imaging on a dataset of 40 CT scans of cystic fibrosis (CF) patients (ages 5-17 years, 65% female). Several possibilities of aerosol diameter and lining fluid thickness were tested. FIG. 22 illustrates that the simulated concentrations of inhaled antibiotic were dependent on patient-related factors. The highest AZLI concentrations were found in the lower lobes. The more diseased lobes were likely to receive lower concentrations of AZLI, hence the method can be used to identify regions in the lungs of CF patients that have been undertreated.

Figure 9A:
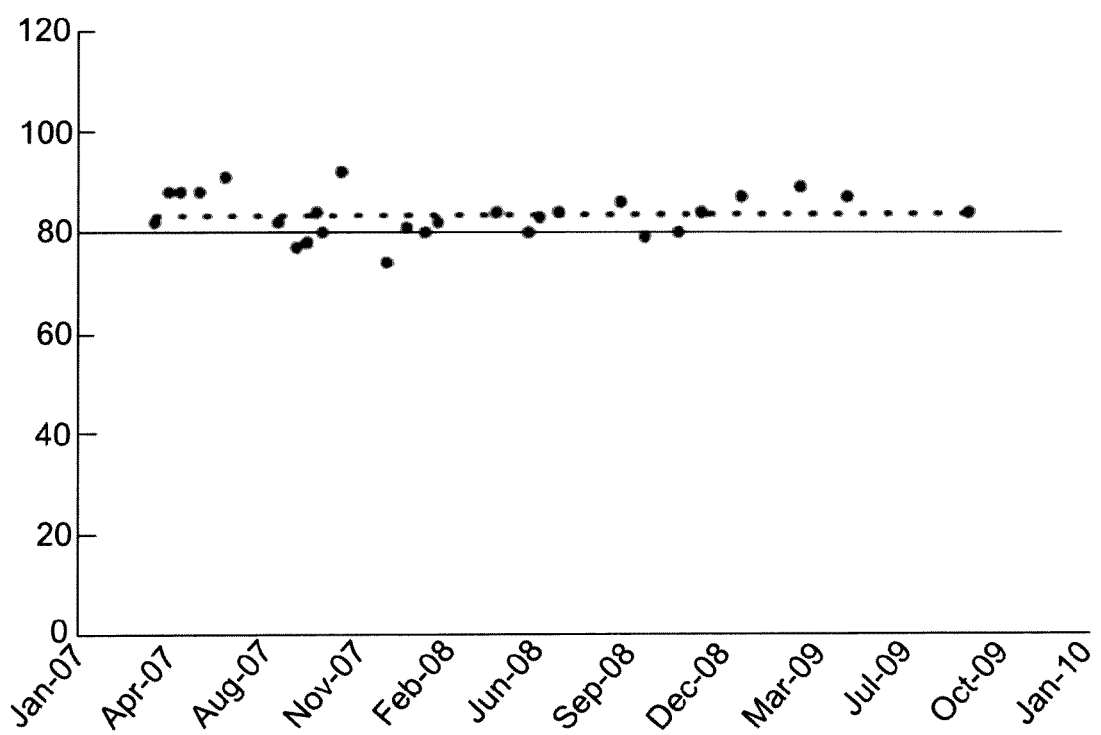
Figure 9B:
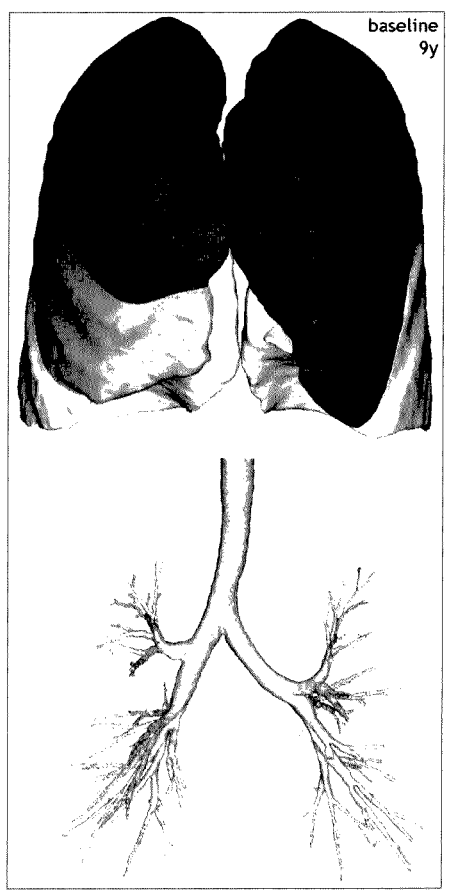
Figure 9C:
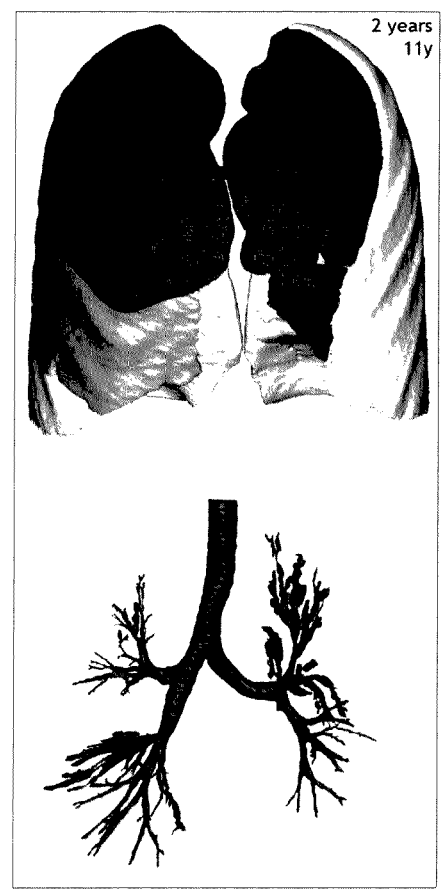
Figure 9D:
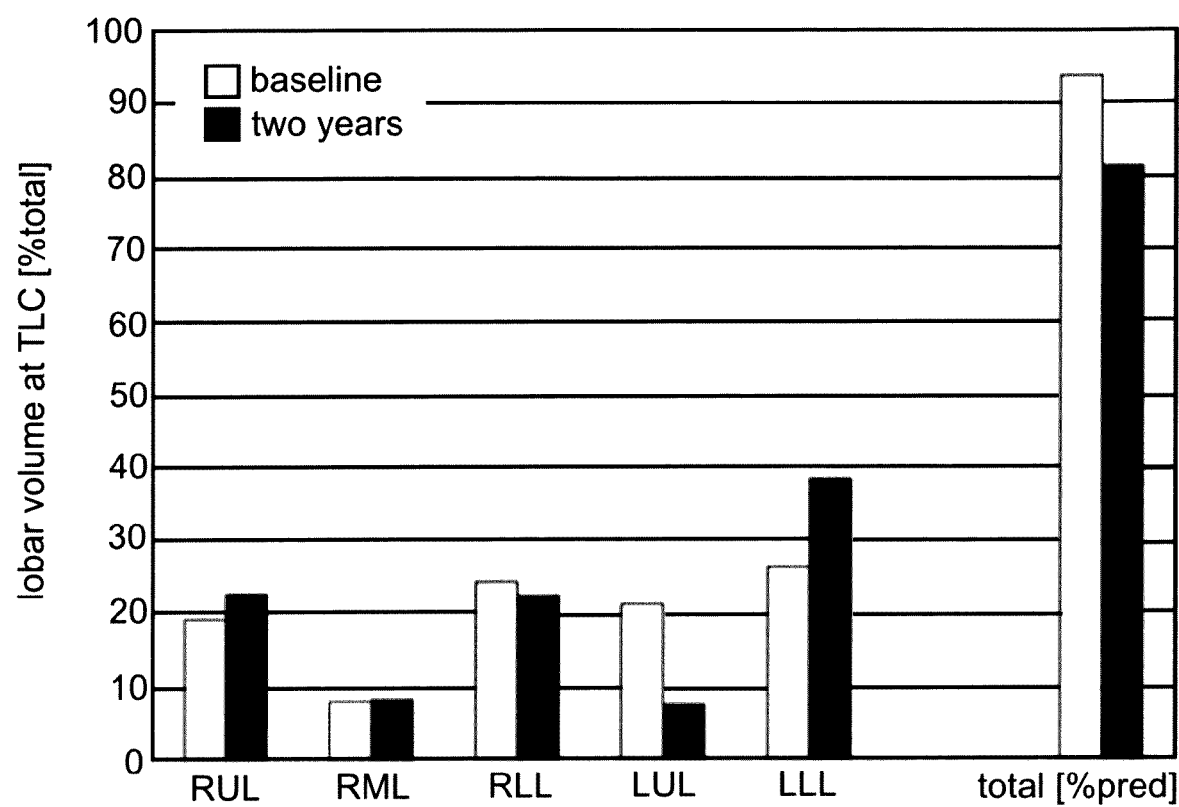
Figures 11A, 11B, 11C:
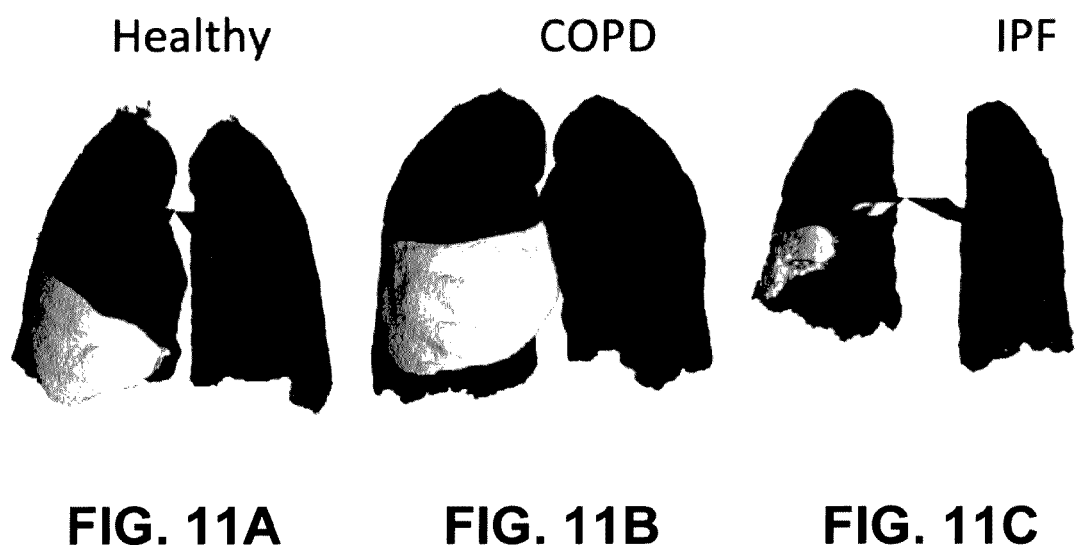

In an embodiment, the method comprises detection of lung functional decline or regional lung functional decline. Regional lung function decline (e.g. on lobar level) cannot be assessed using conventional lung function tests, such as FEV1. FIG. 9A shows the FEV1 value of 9-year-old patient suffering from CF over the course of two years. It can be seen that this parameter, apart from seasonal fluctuations, is very stable. However, FIGS. 9B-E show that the outcome parameters according to the invention indicate a significant decline in the left upper lobe volume as a consequence of severe inflammation of the airways towards this lobe. Apparently the remaining parts of the lung are capable of compensating such that the FEV1 appears stable while in reality the disease manifestation is significant. Preferred outcome parameters for detection of lung functional decline or regional lung functional decline are parameters a, b, e, f, and g. In an embodiment, the method comprises detection of lung functional decline or regional lung functional decline using outcome parameter a. In an embodiment, the method comprises detection of lung functional decline or regional lung functional decline using outcome parameter b. In an embodiment, the method comprises detection of lung functional decline or regional lung functional decline using outcome parameter e. In an embodiment, the method comprises detection of lung functional decline or regional lung functional decline using outcome parameter f. In an embodiment, the method comprises detection of lung functional decline or regional lung functional decline using outcome parameter g.

In an embodiment, the method comprises optimization of an inhalation treatment. As in the previous cases, described above, inhalation treatment and especially inhaled antibiotics need to end up in the correct zones. According to the invention, outcome parameter h can optimize the treatment as will be explained in more detail in the section below on IPF. In an embodiment, the method comprises optimization of an inhalation treatment using outcome parameter h.

In a preferred embodiment, the respiratory condition is related to idiopathic pulmonary fibrosis (IPF). Idiopathic pulmonary fibrosis (IPF) (or cryptogenic fibrosing alveolitis (CFA)[1] or idiopathic fibrosing interstitial pneumonia) is a chronic, progressive form of lung disease characterized by fibrosis of the supporting framework (interstitium) of the lungs. By definition, the term is used only when the cause of the pulmonary fibrosis is unknown ("idiopathic").

In an embodiment, the method comprises detection of lung functional decline or regional lung functional decline. To demonstrate the use of the method according to the invention (particularly the use of parameters a, b, e, f, and/or g) in IPF, the inventors compared a healthy subject with a patient with Chronic Obstructive Pulmonary Disease (COPD) and with an IPF patient. The pulmonary function of these 3 patients as described by the conventional pulmonary function tests was as follows:

Healthy volunteer (43 yo F, 169 cm, 73.2 kg):
   FEV1=110% p; FEV1/VC=84%; FRC=92% p; sRaw=0.81 kPas COPD patient (71 yo M, 168 cm, 62.9 kg)
   FEV1=44% p; FEV1/VC=28%; FRC=139% p; sRaw=3.05 kPas IPF patient (79 yo F, 154 cm, 68 kg)
   FEV1=99% p; FEV1/VC=80%; FRC=57% p; sRaw=0.66 kPas It can be seen that by using conventional pulmonary function tests that rely on a black box approach it is difficult to clearly differentiate the different subjects. The IPF patient, for instance, has near perfect FEV1 measurement. The figures below demonstrate how the method according to the invention can distinguish between the different diseases in much greater detail and hence can be used to detect early onset of inflammation and pulmonary function decline.

FIG. 10 illustrates qualitative, FIG. 10A-C, and quantitative, FIG. 10D, information about the lobar volumes (FRI parameter a) at inspiration (TLC) demonstrating the differences between healthy, COPD and IPF compared to predicted values. FIG. 11 illustrates qualitative, FIG. 10A-C, and quantitative, FIG. 10D, information about the lobar volumes (FRI parameter a) at expiration (FRC) demonstrating the differences between healthy, COPD and IPF compared to predicted values. Both figures FIG. 10 and FIG. 11 demonstrate the star differences in lobar volumes both at expiration and inspiration, and compared to predicted values. Here the restrictive nature of IPF and the hyperinflation in COPD becomes obvious and can be quantified on a lobar level.

FIG. 12 illustrates a qualitative assessment of redistribution of incoming air based on lobar expansion induced by the lung diseases, and demonstrates the internal redistribution of the incoming air by assessing lobar expansion. It can be observed that in this case for COPD and IPF upper and middle lobes receive more compared to the lower lobes. This allows further detailed investigation of the disease manifestation and progression. FIG. 13 shows the differences in specific image-based airway volumes (siVaw), specific image based airway radius (siraw) and specific image-based resistance (siRaw), demonstrating the differences between healthy, COPD and IPF. FIG. 13 demonstrates the hallmark differences between a healthy subject, a COPD patient and an IPF patient. The airway geometry (airway volume and radius) and resistance is depicted. The obstructive nature of COPD becomes clear when assessing the reduction in airway radius and increase in airway resistance compared to the healthy subject. On the other hand, IPF manifests itself by reducing the airway resistance and increasing the airway volume and radius significantly.

FIGS. 23A to 23C demonstrate that changes in lobar volume (FIG. 23A, parameter a), airway volume (FIG. 23B, parameter b), and airway resistance (FIG. 23C, parameter f) are associated with disease progression in IPF determined using FVC. FIG. 23A shows that when FVC is reduced, image based FRC levels decrease. FIG. 23B shows that when FVC is reduced, the airway volume becomes larger. The effect is more pronounced when volumes are made specific. FIG. 23C shows that when FVC is reduced, the impedance becomes less.

Tracking these changes using a sensitive method such as the method according to the invention may assist in detecting early signs of lung function decline or disease manifestation.

Preferred outcome parameters for detection of lung functional decline or regional lung functional decline are parameters a, b, e, f, and/or g. In an embodiment, the method comprises detection of lung functional decline or regional lung functional decline using outcome parameter a. In an embodiment, the method comprises detection of lung functional decline or regional lung functional decline using outcome parameter b. In an embodiment, the method comprises detection of lung functional decline or regional lung functional decline using outcome parameter e. In an embodiment, the method comprises detection of lung functional decline or regional lung functional decline using outcome parameter f. In an embodiment, the method comprises detection of lung functional decline or regional lung functional decline using outcome parameter g.

In an embodiment, the method comprises optimization of an inhalation treatment. Drug deposition was simulated using patient specific geometries and patient specific inhalation profiles. FIG. 14 illustrates the differences in inhalation profiles between healthy subjects, COPD and IPF patients, demonstrating the decline in inhalation profile due to COPD and the short deep inhalation profile observed in IPF. In an embodiment, the method comprises optimization of an inhalation treatment using outcome parameter h.

In a preferred embodiment, the respiratory condition is related to chronic obstructive pulmonary disease (COPD). Chronic obstructive pulmonary disease (COPD), also known as chronic obstructive lung disease (COLD), chronic obstructive airway disease (COAD), chronic airflow limitation (CAL) and chronic obstructive respiratory disease (CORD), is the occurrence of chronic bronchitis or emphysema, a pair of commonly co-existing diseases of the lungs in which the airways narrow over time. This limits airflow to and from the lungs, causing shortness of breath (dyspnea). In clinical practice, COPD is defined by its characteristically low airflow on lung function tests. In contrast to asthma, this limitation is poorly reversible and usually gets progressively worse over time.

In an embodiment, the method comprises detection of lung functional decline or regional lung functional decline. In an embodiment, the method comprises detection of lung functional decline or regional lung functional decline using outcome parameter a. In an embodiment, the method comprises detection of lung functional decline or regional lung functional decline using outcome parameter b. In an embodiment, the method comprises detection of lung functional decline or regional lung functional decline using outcome parameter e. In an embodiment, the method comprises detection of lung functional decline or regional lung functional decline using outcome parameter f. In an embodiment, the method comprises detection of lung functional decline or regional lung functional decline using outcome parameter g.

In an embodiment, the method comprises optimization of an inhalation treatment. In an embodiment, the method comprises optimization of an inhalation treatment using outcome parameter h.

In a preferred embodiment, the respiratory condition is related to asthma. FIG. 24 shows a table presenting data of the effect of bronchodilation on airway volume (iVaw, parameter b) and airway wall thickness (iVaww, parameter e) in asthamatic patients, both parameters yielding a high effect size.

In an embodiment the method comprises detection of lung functional decline or regional lung functional decline. In an embodiment, the method comprises detection of lung functional decline or regional lung functional decline using outcome parameter a. In an embodiment, the method comprises detection of lung functional decline or regional lung functional decline using outcome parameter b. In an embodiment, the method comprises detection of lung functional decline or regional lung functional decline using outcome parameter e. In an embodiment, the method comprises detection of lung functional decline or regional lung functional decline using outcome parameter f. In an embodiment, the method comprises detection of lung functional decline or regional lung functional decline using outcome parameter g.

In an embodiment, the method comprises optimization of an inhalation treatment. In an embodiment, the method comprises optimization of an inhalation treatment using outcome parameter h.

The invention also encompasses the use of the method as described above in clinical trials.

In some preferred embodiments, the method is used in clinical trials. FIG. 18 shows various levels that may be relevant for clinical trials, from mode of action to clinical benefit. However, for more general parameters (such as patient's quality of life), there are a lot of confounding parameters. Therefore, for clinical trials based on such general parameters, the required sample size is very high. For intermediate parameters (such as pulmonary function), there are still many confounding parameters, so the required sample size is still quite high. Only for very detailed parameters obtained by the methods as described above, can the confounding factors be largely eliminated. The methods as described above allow for precise results to be obtained with a much smaller sample size.

As shown in "Wim Vos, Jan De Backer, Gianluigi Poli, Annick De Voider, Liesbeth Ghys, Cedric Van Holsbeke, Samir Vinchurkar, Lieve De Backer, and Wilfried De Backer, *Use of novel functional imaging methods for the assessment of long-term changes in small airways of patients treated with extrafine beclomethasone/formoterol, Respiration* 2013", and "Lieve De Backer, Wim Vos, Jan De Backer, Cedric Van Holsbeke, Samir Vinchurkar, Wilfried De Backer, *Double blind, placebo controlled crossover study in COPD patients to assess the acute effect of budesonide/formoterol using multi-slice CT and lung function tests, Eur Respir J* 2012; 40: 298-305", which are hereby incorporated in their entirety by reference, the signal-to-noise ratio of the methods as described above is much higher than the signal-to-noise ration of conventional methods. This is also illustrated in FIG. 19A (for an asthma population) and 19B (for a COPD population). As shown in FIGS. 20A (asthma) and 20B (COPD), this allows for much smaller sample sizes to be used. FIG. 21 shows an example of a decision tree that may be used to decide whether phase IIb or phase III clinical trials should be started. The decision tree uses input from both conventional pulmonary function tests (PFT) and the method according to the invention, i.e. functional respiratory imaging (FRI). When both PFT and FRI show negative results in the phase IIa clinical trials, the project may be abandoned. When both PFT and FRI show positive results in the phase IIa clinical trials, phase IIB or phase III clinical trials may be started. However, when the results from PFT are inconclusive, yet FRI gives a positive indication, the decision may be made based on additional criteria, as set out below. For example, the signal-to-noise ratio may simply be too low in PFT. As show in *Eur Respir J* 2012; 40: 298-305, as cited above, FRI has a higher signal-to-noise ratio and can yield significant results for smaller sample sizes. In such cases, a conclusive PFT analysis may be obtained by increasing the sample size.

For example, based on FRI phenotyping, the difference may be made between responders and non-responders. The difference between responders and non-responders can be seen in "Jan De Backer, Wim Vos, Cedric Van Holsbeke, Samir Vinchurkar, Rita Claes, Paul Parizel, Wilfried De Backer, *The effect of high dose N acetylcysteine on airway geometry, inflammation and oxidative stress in COPD patients, Int Journal of COPD* 2013:8, p. 569-579", the entirety of which is hereby incorporated by reference.

For example, based on deposition characteristics, a distinction may be made between patient-related differences or device-related differences. This is illustrated in "De Backer et al. *Radiology* 257 (2010) 854-862", "De Backer et al. *Med Eng & Phys* 30 (2008) 872-879"; and "Vinchurkar et al. *Inhalation Toxicology* (2012) 24(2): 81-88". The entirety of these three manuscripts is hereby incorporated by reference.

For example, based on FRI, the effect of dosage can be observed. This is illustrated in and "Lieve De Backer, Wim Vos, Jan De Backer, Cedric Van Holsbeke, Samir Vinchurkar, Wilfried De Backer, *Double blind, placebo controlled crossover study in COPD patients to assess the acute effect of budesonide/formoterol using multi-slice CT and lung function tests, Eur Respir J* 2012; 40: 298-305", the entirety of which is hereby incorporated by reference.

The invention also encompasses the use of the method as described above in as a design tool.

In a preferred embodiment, the method is provided as an online service.

The invention also comprises a computer program, or a computer program product directly loadable into the internal memory of a computer, or a computer program product stored on a computer-readable medium, or a combination of such computer programs or computer program products, for performing the method according to the invention.

Preferably, the invention comprises the following numbered embodiments, as set out below:

1. A method for determining a respiratory condition in a subject or for assessing the efficacy of a treatment for a respiratory condition or for optimizing a treatment protocol for a respiratory condition, the method comprising the steps of:

a) obtaining image data concerning two or more three-dimensional images of the subject's respiratory system, which images have been previously acquired during an assessment period;

b) calculating a specific three-dimensional structural model of the subject's respiratory system from each of the data obtained in step a);

c) comparing the three-dimensional structural models of the subject's respiratory system for each of the image data obtained in step a) to determine a respiratory condition or to assess the efficacy of a treatment for a respiratory condition or to optimize a treatment protocol for a respiratory condition.

2. The method according to embodiment 1 for determining a respiratory condition.

3. The method according to embodiment 1 for assessing the efficacy of a treatment of a respiratory condition or for optimizing a treatment protocol of a respiratory condition.

4. The method according to any of embodiments 1 to 3, wherein the image data of step a) were previously acquired using a CT or MRI scan.

5. The method according to embodiment 4, wherein the image data of step a) comprise CT images at FRC and TLC, preferably high-resolution CT images at FRC and TLC.

6. The method according to any of embodiments 1 to 5, wherein the structural model of step b) is calculated using segmentation principles.

7. The method according to any of embodiments 1 to 6, wherein the specific three-dimensional structural model of the subject's respiratory system comprises a three-dimensional structural model of the subject's lung structure.

8. The method according to any of embodiments 1 to 7, wherein the specific three-dimensional structural model of the subject's respiratory system comprises a three-dimensional structural model of the subject's lobar structure.

9. The method according to embodiment 8, wherein the structural model of step b) is calculated using lobar segmentation.

10. The method according to any of embodiments 1 to 9, wherein the specific three-dimensional structural model of the subject's respiratory system comprises a three-dimensional structural model of the subject's airway structure.

11. The method according any of embodiments 1 to 10, wherein the specific three-dimensional structural model of the subject's respiratory system comprises a three-dimensional structural model of the subject's blood vessel structure.

12. The method according any of embodiments 1 to 11, wherein the specific three-dimensional structural model of the subject's respiratory system comprises a three-dimensional structural model of the subject's airway wall structure.

13. The method according to any of embodiments 1 to 12, wherein the specific three-dimensional structural model of the subject's respiratory system comprises a three-dimensional structural model of the subject's emphysematous regions.

14. The method according to any of embodiments 1 to 13, wherein step b) comprises the step b') calculating one or more outcome parameters from the specific three-dimensional structural model of the subject's respiratory system; and wherein step c) comprises the step c') comparing the outcome parameters for each of the data obtained in step a) to determine a respiratory condition or to assess the efficacy of a treatment for a respiratory condition or to optimize a treatment protocol for a respiratory condition.

15. The method according to embodiment 14, wherein the specific three-dimensional structural model of the subject's respiratory system comprises a three-dimensional structural model of the subject's lobar structure and a three-dimensional structural model of the subject's airway structure, and wherein step b') further comprises the following steps:

b") modeling by a computer, the air flow through the airway, using the three-dimensional structural model of the subject's lobar structure and the three-dimensional structural model of the subject's airway structure; and b'") optionally, modeling by a computer, the structural behavior of the airway and the interaction with the flow, using the three-dimensional structural model of the subject's lobar structure and the three-dimensional structural model of the subject's airway structure.

16. The method according to embodiment 15, wherein the modeling of step b") comprises computational fluid dynamics (CFD), comprising solving the Navier-Stokes equations numerically.

17. The method according to embodiment 16, wherein the three-dimensional structural model of the subject's lobar structure is used to determine boundary conditions for the computational fluid dynamics.

18. The method according to embodiment 17, wherein:
the specific three-dimensional structural model of the subject's respiratory system further comprises a three-dimensional structural model of the subject's lung structure at TLC and FRC; and
the specific three-dimensional structural model of the subject's respiratory system comprises a three-dimensional structural model of the subject's lobar structure at TLC and FRC;
wherein this specific three-dimensional structural model of the subject's respiratory system is used to determine mass flow rate towards each lobe, and subsequently to obtain the boundary conditions for said computational fluid dynamics.

19. The method according to any one of embodiments 14 to 18, wherein the one or more outcome parameters comprise the lobar volume, preferably at FRC and TLC.

20. The method according to any one of embodiments 14 to 19, wherein the one or more outcome parameters comprise the airway volume, preferably at FRC and TLC.

21. The method according to any of embodiments 14 to 20, wherein the one or more outcome parameters comprise lobar emphysema.

22. The method according to any of embodiments 14 to 21, wherein the one or more outcome parameters comprise lobar blood vessel volume.

23. The method according to any of embodiments 14 to 22, wherein the one or more outcome parameters comprise the airway wall thickness.

24. The method according to any of embodiments 14 to 23, wherein the one or more outcome parameters comprise the airway resistance, preferably at FRC and TLC.

25. The method according to any of embodiments 14 to 24, wherein the one or more outcome parameters comprise the airway volume and/or resistance.

26. The method according to any of embodiments 14 to 25, wherein the one or more outcome parameters comprise aerosol deposition characteristics, such as effective lung dose.

27. The method according to any of embodiments 1 to 26, wherein the respiratory condition is related to a lung transplantation.

28. The method according to embodiment 27, wherein method comprises geometrical matching of donor/receptor, preferably by comparing an outcome parameter as defined in any of embodiments 19, 20 or 24.

29. The method according to embodiment 27, wherein method comprises detection of bronchiolitis obliterans (BOS), preferably by comparing an outcome parameter as defined in any of embodiments 19, 20, 22, 23, 24, or 25.

30. The method according to embodiment 27, wherein the method comprises optimization of an inhalation treatment, preferably by comparing an outcome parameter as defined in embodiment 26.

31. The method according to any of embodiments 1 to 26, wherein the respiratory condition is related to radiotherapy.

32. The method according to embodiment 31, wherein the method comprises detection of radiation pneumonitis and/or fibrosis, preferably by comparing an outcome parameter as defined in any of embodiments 19, 20, 23, 24, or 25.

33. The method according to embodiment 31, wherein the method comprises optimization of an inhalation treatment, preferably by comparing an outcome parameter as defined in embodiment 26.

34. The method according to any of embodiments 1 to 26, wherein the respiratory condition is related to cystic fibrosis.

35. The method according to embodiment 34, wherein the method comprises detection of lung functional decline or regional lung functional decline, preferably by comparing an outcome parameter as defined in any of embodiments 19, 20, 23, 24, or 25.

36. The method according to embodiment 34, wherein the method comprises optimization of an inhalation treatment, preferably by comparing an outcome parameter as defined in embodiment 26.

37. The method according to any of embodiments 1 to 26, wherein the respiratory condition is related to idiopathic pulmonary fibrosis (IPF).

38. The method according to embodiment 37, wherein the method comprises detection of lung functional decline or regional lung functional decline, preferably by comparing an outcome parameter as defined in any of embodiments 19, 20, 23, 24, or 25.

39. The method according to embodiment 37, wherein the method comprises optimization of an inhalation treatment, preferably by comparing an outcome parameter as defined in embodiment 26.

40. The method according to any of embodiments 1 to 26, wherein the respiratory condition is related to chronic obstructive pulmonary disease (COPD).

41. The method according to embodiment 40, wherein the method comprises detection of lung functional decline or regional lung functional decline, preferably by comparing an outcome parameter as defined in any of embodiments 19, 20, 23, 24, or 25.

42. The method according to embodiment 40, wherein the method comprises optimization of an inhalation treatment, preferably by comparing an outcome parameter as defined in embodiment 26.

43. The method according to any of embodiments 1 to 26, wherein the respiratory condition is related to asthma.

44. The method according to embodiment 43, wherein the method comprises detection of lung functional decline or regional lung functional decline, preferably by comparing an outcome parameter as defined in any of embodiments 19, 20, 23, 24, or 25.

45. The method according to embodiment 43, wherein the method comprises optimization of an inhalation treatment, preferably by comparing an outcome parameter as defined in embodiment 26.

46. The method according to any of embodiments 1 to 45, wherein the method is provided as an online service.

47. A computer program, or a computer program product directly loadable into the internal memory of a computer, or a computer program product stored on a computer-readable medium, or a combination of such computer programs or computer program products, for performing the method according to any of embodiments 1 to 45.

48. Use of the method according to any of embodiments 1 to 46 in clinical trials.

The invention claimed is:

1. A method for determining lung function in a subject suffering from a respiratory condition, the method comprising the steps of:
   a) obtaining image data concerning two or more three-dimensional computed tomography (CT) images of the subject's respiratory system, wherein the images are acquired during an assessment period comprising a breathing cycle, and wherein the breathing cycle comprises at least functional residual capacity (FRC) and total lung capacity (TLC);
   b) calculating a specific three-dimensional structural model of the subject's respiratory system for each of the two or more three-dimensional images of step a), the specific three-dimensional structural model of the subject's respiratory system comprising a three-dimensional structural model of the subject's lobar structure at each of TLC and FRC, and a three-dimensional structural model of the subject's airway structure at each of TLC and FRC, wherein step b) further comprises the steps of:
   b') modeling, by a computer, an air flow through the subject's airway structure by determining a mass flow rate towards each lobe of the subject's lobar structure, using the three-dimensional structural models of the subject's lobar structure, and, using the determined mass flow rates as boundary conditions, performing computational fluid dynamic (CFD) numerical analysis using Navier-Stokes equations to model the air flow;
   b") modeling, by the computer, a structural behavior of the subject's airway structure and an interaction of the airway structure with the air flow, using the three-dimensional structural models of the subject's lobar structure and the three-dimensional structural models of the subject's airway structure; and
   b''') calculating one or more outcome parameters from b') and b") for each of the specific three-dimensional structural models of the subject's respiratory system, wherein the one or more outcome parameters comprises lobar blood vessel volume, and optionally one or more of lobar volume, airway volume, airway wall thickness, and airway wall resistance; and
   c) determining a respiratory condition by comparing the outcome parameters at step b''') at TLC and at FRC.

2. The method according to claim 1, wherein the respiratory condition is related to a lung transplantation.

3. The method according to claim 1, wherein the respiratory condition is related to cystic fibrosis.

4. The method according to claim 3, wherein the method comprises detection of lung functional decline or regional lung functional decline.

5. The method according to claim 1, wherein the respiratory condition is related to idiopathic pulmonary fibrosis (IPF).

6. The method according to claim 5, wherein the method comprises detection of lung functional decline or regional lung functional decline.

7. The method according to claim 1, wherein the respiratory condition is related to chronic obstructive pulmonary disease (COPD).

8. The method according to claim 7, wherein the method comprises detection of lung functional decline or regional lung functional decline.

9. The method according to claim 1, wherein the respiratory condition is related to asthma.

10. The method according to claim 9, wherein the method comprises detection of lung functional decline or regional lung functional decline.

11. The method according to claim 1, wherein the method comprises detection of lung functional decline or regional lung functional decline.

12. The method according to claim 1, wherein the method comprises optimization of an inhalation treatment.

13. The method according to claim 1, wherein the respiratory condition is related to sarcoidosis.

14. The method according to claim 1, wherein the respiratory condition is related to radiation fibrosis.

* * * * *